(12) United States Patent
Winstrom

(10) Patent No.: US 6,506,402 B1
(45) Date of Patent: Jan. 14, 2003

(54) CHLORTETRACYCLINE-CONTAINING ANIMAL FEED COMPOSITIONS AND METHODS FOR THEIR USE

(75) Inventor: Willis L. Winstrom, Omaha, NE (US)

(73) Assignee: Pennfield Oil Company, Omaha, NE (US)

(*) Notice: Subject to any disclaimer, the term of this patent is extended or adjusted under 35 U.S.C. 154(b) by 0 days.

(21) Appl. No.: 09/587,411

(22) Filed: Jun. 5, 2000

Related U.S. Application Data

(63) Continuation-in-part of application No. 09/350,474, filed on Jul. 9, 1999.
(60) Provisional application No. 60/103,074, filed on Oct. 5, 1998, provisional application No. 60/105,229, filed on Oct. 21, 1998, and provisional application No. 60/115,761, filed on Jan. 13, 1999.

(51) Int. Cl.[7] .......................... A61F 13/00; A23L 1/36; A23B 7/10; C12P 33/20
(52) U.S. Cl. .................... 424/442; 426/633; 426/53; 426/54; 435/48
(58) Field of Search ............... 426/633, 53, 54; 424/80; 435/48

(56) References Cited

U.S. PATENT DOCUMENTS

| | | | | |
|---|---|---|---|---|
| 4,081,527 A | * | 3/1978 | Armstrong | 424/80 |
| 5,266,347 A | * | 11/1993 | King | 426/623 |

OTHER PUBLICATIONS

Waldroup, "Feeds and Feed Additives, Nonruminant Feeds", 1994.*

* cited by examiner

*Primary Examiner*—José G. Dees
*Assistant Examiner*—Robert M. DeWitty

(74) *Attorney, Agent, or Firm*—Suiter & Associates PC; Scott C. Rand; William J. Breen, III

(57) ABSTRACT

The present invention provides improved chlortetracycline-containing animal feed compositions and processes and apparatuses for their preparation. In certain embodiments, raw fermentation broth comprising chlortetracycline is divided into two portions. The first portion is mixed with a compound that complexes chlortetracycline. The second portion is acidified and the solids are removed. The acidified liquid is treated with a complexing agent to produced a chlortetracycline complex. The first and second portions thus treated are then mixed and the mixture is passed on to a filter press or other means for separation of the solids to produce a wet cake comprising complexed chlortetracycline. In alternative embodiments, the second portion may be acidified and filtered and admixed with the first portion prior to the complexing step. The resulting mixture is passed on to a filter press or other means for separation of the solids. In still further embodiments, the complexing steps are replaced with neutralizing or basification steps to yield the free base form of chlortetracycline. The wet filter cake comprising chlortetracycline and fermentation solids is dried and sized to produce a dried semi-finished product in the form of a powder, meal, granules, pellets, tablets, etc. The semi-finished product may be standardized to produce an animal feed supplement having a desired potency. In a further aspect, the present invention relates to a method of combating microbial infection and promoting growth in animals comprising orally administering to said animals an effective amount of an animal composition according to the present invention.

104 Claims, 6 Drawing Sheets

US 6,506,402 B1

CHLORTETRACYCLINE-CONTAINING ANIMAL FEED COMPOSITIONS AND METHODS FOR THEIR USE

RELATED APPLICATION

This is a continuation-in-part of U.S. application Ser. No. 09/350,474, filed Jul. 9, 1999.

INCORPORATION BY REFERENCE

Each of the following applications are incorporated herein by reference in its entirety: provisional U.S. application No. 60/103,074 filed Oct. 5, 1998, No. 60/105,229, filed Oct. 21, 1998, No. 60/115,761, filed Jan. 13, 1999, and U.S. application Ser. No. 09/350,474, filed Jul. 9, 1999, and Ser. No. 09/587,410, filed on even date herewith.

FIELD OF THE INVENTION

The present invention relates to an improved process for the preparation of chlortetracycline-containing compositions suitable for incorporation in animal feed.

BACKGROUND OF THE INVENTION

Antibiotics, such as tetracyclines, are used as growth promoters and feed efficiency promoters in animals such as poultry and livestock, and for therapeutic and prophylactic disease control in animals such as poultry and livestock, fish, domesticated pets, and so forth. Such antibiotics are typically formulated in an animal feed premix or animal feed supplement containing the antibiotic and an edible carrier or diluent. These premixes or animal feed supplements may then be mixed with a sufficient quantity of an appropriate animal feed (e.g., livestock, poultry, fish, pet and/or other animal feed) to provide a final animal feed formulation having the desired level of active compound in the feed.

Prior art chlortetracycline-containing animal feed supplements prepared through normal fermentation and dehydration of the mycelium meal provide, at maximum, chlortetracycline potencies of about 26% to 28% by weight. The highest concentration currently available in a standardized feed supplement is 22%. (Since chlortetracycline hydrochloride is the reference standard for chlortetracycline feed grade materials, all chlortetracycline concentrations and percentages stated herein, unless indicated otherwise, are calculated as the hydrochloride equivalent, regardless of the form present (e.g., the free base, complexes or salts other than the hydrochloride, etc.) In order to obtain higher chlortetracycline concentrations, it is possible add pure crystalline chlortetracycline hydrochloride USP to the mycelium meal to raise the potency. This, however, is not economical. Furthermore, because chlortetracycline hydrochloride is water soluble, there is a question of stability in finished feeds containing moistures of 10% or higher.

It would therefore be desirable to provide a chlortetracycline-containing animal feed premix or animal feed supplement suitable for use in the veterinary, animal nutrition, and animal husbandry arts that can be prepared directly from a fermentation product and that can be prepared in a high concentration without requiring the addition of the antibiotic in pure form and that has improved stability over chlortetracycline hydrochloride feed supplements.

SUMMARY OF THE INVENTION

The present invention provides an improved process and apparatus for the preparation of a fermentation cake or mycelium meal material containing chlortetracycline. The present invention also relates to the chlortetracycline-containing fermentation cake or mycelium meal material so produced and chlortetracycline-containing animal feed additives derived therefrom. It has been discovered that the procedures in accordance with this teaching produce chlortetracycline-containing fermentation products having higher concentrations than possible from prior fermentation/dehydration processes, thus making it possible to produce animal feed supplements which take up less room in feed complexes, require less storage space, reduce packaging and shipping costs, and so forth. The present invention also relates to animal feed compositions prepared in accordance with this teaching.

In certain embodiments, the present invention provides chlortetracycline-containing animal feed additives having a chlortetracycline concentration of about 35% or greater. In preferred embodiments, the present invention provides chlortetracycline-containing animal feed additives having a chlortetracycline concentration of about 40% to about 70%, or greater. In more preferred embodiments, the present invention provides chlortetracycline-containing animal feed additives having a chlortetracycline concentration of about 44% to about 55%.

In additional embodiments, the present invention also relates to methods for preventing or combating microbial infection in animals comprising orally administering to said animals a prophylactic or therapeutic amount of an animal comestible composition comprising a medicated feed supplement according to the present invention. In yet a further embodiment, the present invention relates to methods for increasing feed efficiency, promoting animal growth, and increasing rate of weight gain and in an animal comprising orally administering to said animals an effective amount of an animal comestible composition comprising a medicated feed supplement according to the present invention.

It is to be understood that both the foregoing general description and the following detailed description are exemplary and explanatory only and are not restrictive of the invention as claimed. The accompanying drawings, which are incorporated in and constitute a part of the specification, illustrate various embodiments of the invention and together with the general description, serve to explain the principles of the invention.

BRIEF DESCRIPTION OF THE DRAWING

The numerous objects and advantages of the present invention may be better understood by those skilled in the art by reference to the accompanying figures in which.

DETAILED DESCRIPTION OF THE INVENTION

Figure 1:
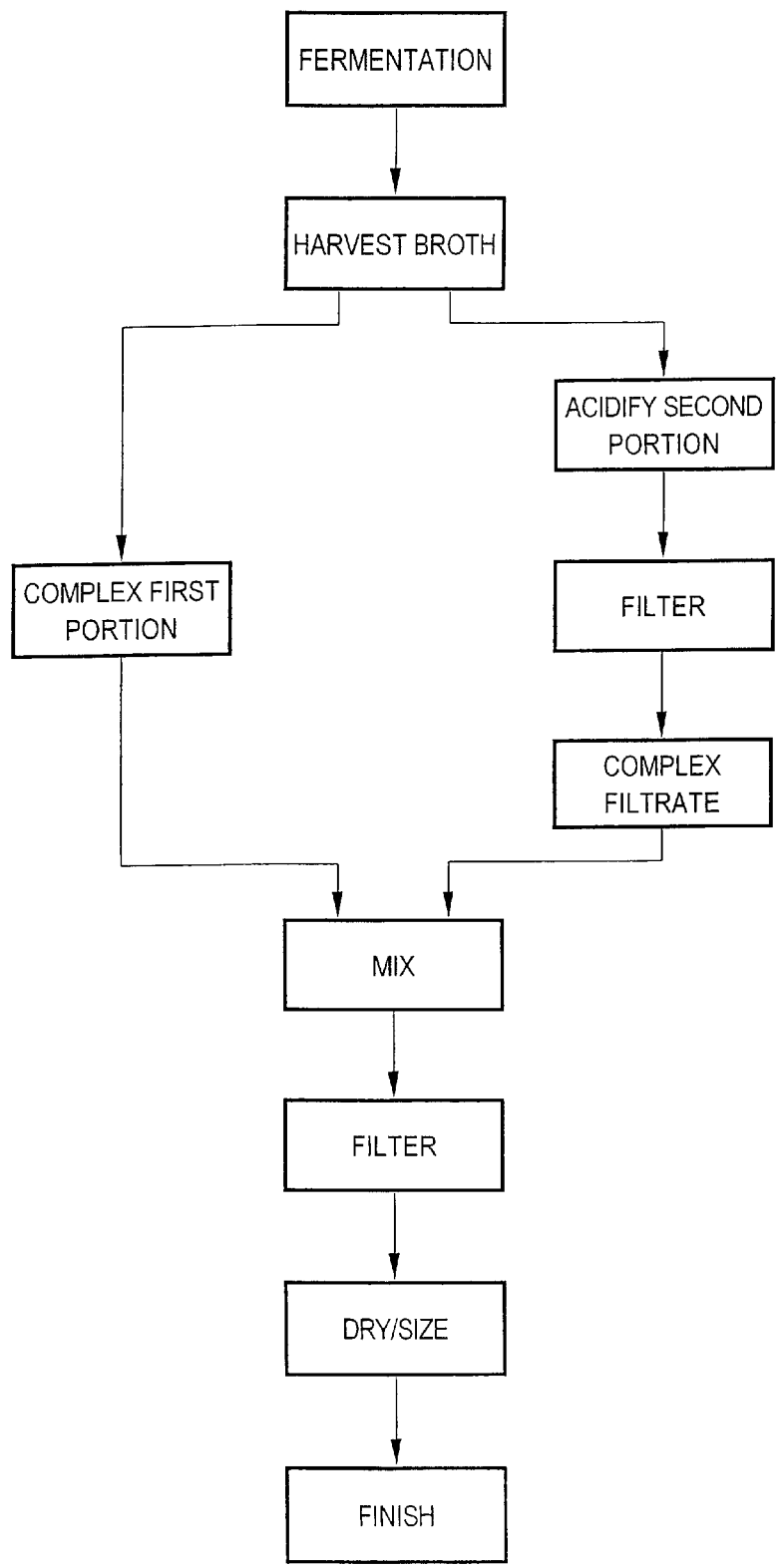
FIGS. 1 and 2 are flow charts outlining processes for preparing a chlortetracycline-containing animal feed composition in accordance with two embodiments of the present invention wherein the chlortetracycline is present in the form of a complex.

The chlortetracycline animal feed supplements in accordance with the present invention are prepared by fermentation of a microbial source organism that produces chlortetracycline, including but not limited to *Streptomyces aureofaciens*, as is generally known in the art. The fermentation process may be any suitable fermentation process, and may be a commercial or industrial scale fermentation process. Generally, an inoculum is started by collecting the spores of a chlortetracycline producing organism such as *Streptomyces aureofaciens* or any other chlortetracycline producing species which are germinated to produce an actively growing culture of the microbial source organism. A sterilized, e.g., autoclaved, agar slant or other slant medium is inoculated with the actively growing culture and incubated. The spores produced are then placed into a small amount of liquid, e.g., distilled water, nutrient medium, etc., to produce an aqueous spore suspension which is propagated to produce the inoculum for the fermentation operation. The resulting inoculum is introduced into a fermentation medium to produce a fermentation broth comprising the fermentation medium and inoculum whereby the chlortetracycline is produced by fermentation in the fermentation broth. In one embodiment, an inoculum may be prepared in an insemination fermentor in a suitable nutrient medium, and the inoculum thus prepared may be transferred to an industrial fermentor.

Cultivation of *Streptomyces aureofaciens* or other source organism may be carried out in a wide variety of liquid media. Media which are useful for the production chlortetracycline include an assimilable source of carbon and an assimilable source of nitrogen. Assimilable or metabolizable sources of carbon and nitrogen are generally known in the art. Exemplary of sources of carbon include, for example, glucose or other sugars, including sucrose, maltose, dextrose, and the like, polysaccharide, starches such as corn starch, potato starch or the like, molasses, glycerol, sugar alcohols, oil and fats, and so forth. Exemplary sources of nitrogen include, for example, protein, protein hydrolysates (e.g., peptones), polypeptides, amino acids, corn steep liquor, beef or other meat extracts, soy protein products (e.g., isolates, flours, meals, etc.) yeast protein (e.g., yeast extracts, yeast autolysates, etc.), casein (hydrolyzed or unhydrolyzed), fish meal, urea, nitrates, ammonia, and various other nitrogenous substances of plant or animal origin. Other ingredients may be supplied as necessary, and in many cases may be present in the nitrogen source or other constituents of the media, including enzymes, complex growth factors (e.g., vitamins), inorganic anions and cations, such as potassium, sodium, ammonium, calcium, sulfate, carbonate, phosphate, chloride, etc., and trace elements such as boron, molybdenum, copper, cobalt, iron, copper, zinc, etc.

Oxygen is supplied to the medium during fermentation. Aeration is provided by forcing sterile air through or onto the surface of the fermenting medium. Although aeration alone may provide the desired agitation, further agitation is generally desirable, e.g., as provided by a mechanical impeller located within the vessel. An anti-foaming agent such as a vegetable oil, lard oil, silicone defoamer, hydrocarbon petroleum, and the like may be added to control foaming as needed.

The fermentation medium is brought to a temperature of about 25° C. to about 40° C., preferably about 28° C. to about 35° C., The length of time that the fermentation process is allowed to continue depends on the a number of factors, including the composition of the fermentation medium, temperature, quantity of cells in the inoculum, quantity and/or concentration of chlortetracycline desired in the fermentation broth, and the ability to avoid contamination of the fermentation medium with other cultures. Typically, for batch-wise production, the fermentation time can vary from about 50 hours to about 200 hours.

It will be recognized that the present invention may also be implemented using a continuous fermentation process. After chlortetracycline production achieves a steady state, chlortetracycline production may be maintained by the continuous addition of fermentation medium (e.g., without addition of new inoculum) and continuous removal of fermentation broth at a rate such that the volume of fermentation broth in the fermentation tank and the concentration of chlortetracycline in the fermentation broth remain essentially constant. Alternatively, the removal and addition may be performed in intermittent fashion rather than continuously so long as the average broth volume remains essentially constant. The production rate may be adjusted by control of the medium composition and other fermentation conditions, as well as the rate of addition and removal, so as to optimize or provide a desired rate of chlortetracycline production. In theory, continuous chlortetracycline production can continue indefinitely, however, in practice, it is limited by contamination of the fermentation medium with other microorganisms, equipment malfunction, abnormalities in the process, and so forth. Continuous production may be continued for up to several weeks or longer, or until chlortetracycline production decreases to an uneconomical level.

The certain embodiments, an appropriate amount of fermentation medium containing the entire amount of carbon and nitrogen source material to be consumed during the fermentation process may be added to the fermentation tank at the beginning of the fermentation process. However, it has been found in accordance with this teaching that the further addition of nitrogen source materials after fermentation has begun increases potency by 5% or more. The additional nitrogen source may be added by a number of methods. In certain embodiments, an appropriate amount of nitrogen source material may be initially added to the fermentation medium and addition is continued after the fermentation has begun. In certain embodiments, a single quantity of nitrogen source material may be added after a predetermined period of time, such as 12, 24, 36, 48, etc., hours after the fermentation is begun, or when the nitrogen level in the fermentation medium drops below some predetermined level. In other embodiments, the additional nitrogen source is added as an intermittent series of additions, for example, at predetermined time intervals, or when the nitrogen level in the fermentation medium drops below some predetermined level. For example, in preferred embodiments, relatively small, frequent additions of a nitrogen source material are made. The additions are in an amount sufficient to maintain the nitrogen level within a desired range. The frequency may be, for example, half-hourly (or more frequently) to about bihourly, preferably hourly. In still other embodiments, the additional nitrogen source is added continuously, beginning at the time the fermentation is begun, at some period of time after the fermentation is begun, or when the nitrogen level in the fermentation medium drops below some predetermined level. The additional nitrogen source material is added to the fermentor in such a quantity and/or rate that will maintain the nitrogen concentration at or above the minimum level required for fermentation. Typically, the additional nitrogen is added so that the nitrogen concentration is maintained at about 30–300 mg/100 mL, more typically about 60–120 mg/100 mL.

Additional carbon source material may also be added during the fermentation operation. Similarly, a single quantity of carbon source material may be added after a predetermined period of time, such as 12, 24, 36, 48, etc., hours after the fermentation is begun, or when the carbon level in the fermentation medium drops below some predetermined level. In other embodiments, the additional carbon source is added as an intermittent series of additions, for example, at predetermined time intervals, or when the carbon level in the fermentation medium drops below some predetermined level. For example, in preferred embodiments, relatively small, frequent additions of a carbon source material are made. The additions are in an amount sufficient to maintain the assimilable carbon level within a desired range. The frequency may be, for example, half-hourly (or more frequently) to about bihourly, preferably hourly. In still other embodiments, the additional carbon source is added continuously, beginning at the time the fermentation is begun, at some period of time after the fermentation is begun, or when the carbon level in the fermentation medium drops below some predetermined level. The additional carbon source material is added to the fermentor in such a quantity and/or rate that will maintain the carbon concentration at or above the minimum level required for fermentation. Typically, the additional carbon source or sources are added so that the amount of carbon source material in the fermentation medium concentration is maintained at about 0.1% to about 10% by weight, more typically about 0.5% to about 5% by weight.

When the concentration of chlortetracycline reaches the desired level in the fermentation broth, the fermentation broth, including the biomass and other fermentation solids, is harvested and divided into two portions. It is not necessary that a single fermentation batch be divided into two portions and alternatively, the two portions may be harvested from two or more fermentation tanks. Likewise, the two portions may be derived separate batches of a single fermentor wherein one portion is derived from a first fermentation batch and the second portion is derived from a subsequent fermentation batch. For the sake of brevity, the present invention will be shown and described herein primarily by way of reference to harvesting the fermentation broth from a single fermentation tank and dividing the harvested broth into two portions, however, it will be recognized that such teachings are intended to encompass and are equally applicable to obtaining the first and second portions from a plurality of fermentation tanks or a plurality of fermentation batches obtained from a single fermentor.

The first portion of the harvested fermentation broth is sent to a mixing tank. If the finished feed supplement is to contain chlortetracycline as the free base, the harvested fermentation broth may be treated with a base, such as ammonia, in an amount to neutralize the chlortetracycline. In forming the free base form of chlortetracycline, any base known to those skilled in the art can be used to neutralize the chlortetracycline-containing to form the free base form of chlortetracycline. Preferably, the base is an aqueous ammonia solution. Other exemplary bases include but are not limited to alkali metal hydroxides, preferably aqueous solutions thereof, such as aqueous sodium hydroxide. If the finished feed supplement is to contain complexed chlortetracycline, the harvested fermentation broth is admixed with a compound that complexes chlortetracycline, preferably in an amount sufficient to completely complex the tetracycline.

The second portion of the fermentation broth is sent to an acidification tank for treatment with an acid and dilution. The acidified broth is then passed on for separation of the solids. The separation may be performed in a number of ways, including filtration, centrifuging, siphoning, decanting, pumping off, evaporation, and so forth. In one embodiment, the filtration is carried out in a filter press or rotary vacuum filter. In a preferred embodiment, the fermentations solids are separated by pumping the fermentation broth through a filter press or with a centrifuge. The filtrate is optionally recycled to the filter for a second filtration.

The filtrate containing the chlortetracycline acid addition salt is passed on to a precipitation tank for precipitating the chlortetracycline. If the finished feed supplement is to contain chlortetracycline as the free base, precipitation is performed by neutralizing the chlortetracycline acid addition salt to form the chlortetracycline free base through addition of a sufficient quantity of a base such as ammonia or other base. Alternatively, if the finished feed supplement is to contain complexed chlortetracycline, precipitation is performed by adding a complexing agent, preferably in an amount substantially sufficient to completely complex the chlortetracycline.

Where the fined feed supplement contains complexed chlortetracycline, suitable complexing agents are those having the ability to complex with the chlortetracycline at stable pH ranges. Exemplary complexing agents include but are not limited to salts and bases of calcium, magnesium, aluminum, iron, manganese, zinc, and copper, preferably metal salts which exhibit alkaline behavior in aqueous media, e.g., salts of weak acids. Preferred complexing agents include alkaline earth metal carbonates such as magnesium carbonate and calcium carbonate, basic alkaline earth metal compounds such as calcium hydroxide, magnesium hydroxide, calcium chloride, magnesium chloride, calcium oxide, magnesium oxide, calcium sulfate, magnesium sulfate, calcium phosphate, magnesium phosphate, and so forth. The preferred complexing compound is calcium carbonate. The amount of complexing agent needed can be readily determined by those skilled in the art.

The first and second portions, treated as described above, are then mixed and this mixture is then passed for separation of the solids. Separation of the solids, such as filtration, centrifugation, evaporation, or other solid-liquid separation technique, yields a wet fermentation cake comprising chlortetracycline (either as the free base or as a complex), the fermentation biomass and other fermentation solids.

It is not necessary that the first and second portions be separately precipitated prior to admixture. In an alternative embodiment the harvested raw fermentation broth is again divided into first and second portions. The first portion is left in its raw state and the second portion of the fermentation broth is sent to an acidification tank for treatment with an acid as described above. The acidified broth is then passed on for separation of the solids as described above.

The acidified filtrate containing the chlortetracycline activity from the second portion is then mixed with the first portion of the fermentation broth in its raw state. If the finished feed supplement is to contain chlortetracycline as the free base, the resulting mixture is treated with a base, such as ammonia or other base, in an amount sufficient to neutralize the chlortetracycline. If the finished feed supplement is to contain complexed chlortetracycline, the harvested fermentation broth is admixed with a compound that complexes chlortetracycline as detailed above, preferably in an amount sufficient to completely complex the tetracycline. The mixture containing precipitated chlortetracycline (free base or complex) is then passed for separation of the solids as described above.

The wet filter cake (biomass) produced in accordance with the present invention containing precipitated chlortetracycline is then dried and sized. The drying step may be performed by any conventional technique, which may involve the use of any suitable drying means, such as an oven, tray dryer, tunnel dryer, spray dryer, spray granulator, fluid bed dryer, shelf dryer, drum dryer, rotary dryer, microwave dryer, contact dryer, and the like.

The wet cake may optionally be subjected to a compression or compaction step, e.g., to produce pellets, tablets, sheets, ribbons, briquets, extrudates of a desired cross-sectional size and shape, etc., which may optionally be subjected to further size reduction as needed. The optional compaction step may involve the use of any suitable compacting or compressing means, such as a pellet press or pellet mill, punch and die tableting equipment, compression or compaction rollers, extruders, and the like. The compaction or compression step may be performed prior to drying or at an intermediate drying stage, (e.g., paste, slurry, etc.), or after drying. Where a compaction or compression step is used, there may optionally be added one or more fillers, binders, humectants, disintegrating agents, solution retarding agents, absorption accelerators, wetting agents, absorbents, lubricants, or other excipients or carriers as would be known to those skilled the veterinary, animal nutrition, and animal husbandry arts.

The sizing step may be performed by any conventional technique to produce a chlortetracycline-containing semi-finished product having a desirable particle size or range of particle sizes. The desired particle size of the semi-finished product will generally depend on the intended application for the feed supplement. The particle size may range from finely divided powders to relatively coarse particles or granules, for example, having a diameter of up to about 5 mm or larger. Such forms include powder, meal, pellet, granule, tablet, or other similar forms. In certain embodiments, a drying method may be selected that gives the desired particle size (for example, spray drying to a powder) or that gives oversized particles that can be further reduced in size (for example, tray drying the filter cake in tact or in relatively large pieces). Oversize particles may then be further reduced in size to granules or a powder by grinding, milling, screening, pulverizing, crushing, machining, and so forth.

In certain other embodiments, the selected drying method may produce particles that are smaller than desired, in which case the small particles can be built up into larger particles, for example, via an agglomeration process, or via a compaction or compression process as described above. For example, a powder (e.g., produced by spray drying or by mechanically reducing larger particles) may be made into pellets or granules by agglomeration. Alternatively, undersized particles may be compacted, compressed, extruded, etc., as described above.

The sized particles may be subjected to further drying stages after sizing, for example, where the sizing step involves introduction of water (e.g., agglomeration using water) or where the particles are sized before the desired degree of dryness is achieved.

A drying and/or sizing process may produce a distribution of particle sizes wherein only a portion of the particles are within the desired range of particle sizes. In such cases, the oversized and undersized particles may be removed, e.g., by screening. The oversized particles may be further reduced in size as described above and undersized particles may be built up into larger particles via agglomeration, compression or compaction as described above. Alternatively, the undersized particles may be screened and used to increase the chlortetracycline concentration in subsequent harvested fermentation batches.

In certain embodiments, the dry cake is then sized by grinding, milling, pulverizing, screening, etc., to provide the complexed chlortetracycline-containing fermentation solids in particulate form. The particles are screened to produce a semi-finished product having a desired particle size and it has been discovered that the particles so produced provide a solid particulate feed material having good strength and fracture toughness without compression or compaction of the particles.

After drying and sizing, the semi-finished product containing chlortetracycline complex or free base may optionally be standardized to produce a finished product having a desired potency by adding one or more of a diluent, such as one or more of an edible feed material, a mineral product, and an oil.

The term "semi-finished product" is used herein to refer to the product resulting from drying and sizing the filter cake and the term "finished product" is used herein to refer to a product resulting from admixture of the semi-finished product and one or more diluents (e.g., one or more of an edible feed material, a mineral product, and an oil) to provide an animal feed premix having a predetermined or standardized concentration of the active ingredient. It will be recognized, however, that the semi-finished product itself, once assayed for chlortetracycline activity, is itself also suitable for use as an animal feed premix.

The terms "animal feed premix," "animal feed supplement," and "animal feed additive" are generally used herein interchangeably, without attention to any nuances in meaning, to mean a concentrated additive premix comprising chlortetracycline which may be added to an animal's feed to form a medicated comestible composition in accordance with the present invention. The terms "final feed mixture" or "final feed product" will generally be used herein to mean an animal comestible comprising an animal's feed and a medicated animal feed supplement according to the present invention.

The animal feed supplements according to the present invention may be blended with an animal feed to produce a medicated finished complete or supplement feed product. Animals to which the feed supplements according to the present invention may be administered include pets or companion animals, and ranch or farm animals or other livestock, such as animals raised as a food source or other commercial purpose. Such animals include, but are not limited to, cattle, sheep, horses, pigs, buffalo, goats, dogs, cats, rabbits, rats, mice, minks, fish, and fowl (including egg-laying or edible fowl, such as chickens, turkeys, geese, ducks, quail, pheasant, etc.), and so forth.

The medicated animal final feed mixtures according to the present invention are prepared by adding an animal feed premix prepared in accordance with the present invention to an animal's food. The premix may be added to the food in a number of ways. The feed premix containing a given quantity of chlortetracycline may be added to a given quantity of feed and mixed or blended to provide a substantially homogeneous medicated feed composition. Large feed lots may be prepared in this manner for treating a large number of animals. Alternatively, feed batches containing feed for a single animal or single meal may be prepared either by mixing a predetermined quantity of premix according to the present invention with the animal feed or by adding a predetermined quantity of premix to an animal's feed as a top dressing.

By varying the quantity of feed supplement added to the feed, the concentration of the active ingredient in the final feed mixture may be adjusted to meet particular needs and may be varied over a wide range. The minimum concentration should be such as to achieve the desired result (therapeutic, prophylactic, growth enhancement, etc.). The maximum concentration should be such as to avoid any undesirable side effects when the feed rations are ingested by the animal. Within these limitations, specific amounts of active ingredient will normally be regulated by the practitioner according to potency of the premix and the usual recommended dosing levels for the active ingredient. The practitioner will generally take into account a number of factors, such as the animal species being treated, the animal's age or stage of development, the frequency of administration, whether the composition is being administered therapeutically or prophylactically and the degree of antimicrobial results sought, the severity of any disease being treated, and so forth. The selection of dosages and dosage regimens is generally performed as a routine matter by persons skilled in the arts pertaining to veterinary medicine, animal husbandry and nutrition, and the like. Accordingly, the indications and dosage levels given herein are intended to be exemplary and illustrative only, and are not intended to be exhaustive or restrictive of the present invention as claimed.

In a preferred aspect, the present invention provides a semi-finished product having a concentration higher than can be achieved through normal fermentation and dehydration means. In certain embodiments, the semi-finished product has a chlortetracycline concentration of about 35% or greater. In preferred embodiments, the present invention provides semi-finished product having a chlortetracycline concentration of about 40% to about 80%, or greater. In more preferred embodiments, the present invention provides chlortetracycline-containing animal feed additives having a chlortetracycline concentration of about 50% to about 70%.

The semi-finished product in accordance with the present invention may be standardized as described above to provide an animal feed supplement having a desired or predetermined activity. In certain embodiments, the present invention provides chlortetracycline-containing animal feed additives having a chlortetracycline concentration of about 35% or greater. In preferred embodiments, the present invention provides chlortetracycline-containing animal feed additives having a chlortetracycline concentration of about 40% to about 60%, or greater. In more preferred embodiments, the present invention provides chlortetracycline-containing animal feed additives having a chlortetracycline concentration of about 44% to about 55%.

In some of the embodiments according to the present invention, the animal feed supplements according to the present invention will contain a chlortetracycline concentration ranging from about 10 g/lb to about 300 g/lb, and preferably from about 90 g/lb to about 200 g/lb.

Thus, in formulating the final animal comestible feed comprising the animal feed premix according to the present invention to contain the proper amount of active ingredient, one may calculate the amount of active ingredient it is desired to administer to each animal, take into account the amount of feed per day normally consumed by the animal, and compute the proper concentration of chlortetracycline needed in the feed, and add the appropriate amount of animal premix to achieve the proper concentration of chlortetracycline in the final feed mixture.

In some of the preferred embodiments according to the present invention, the final feed comprising an animal feed and the animal feed supplement in accordance with the present invention will generally contain chlortetracycline in an amount of about 0.1 g/ton or greater, generally ranging from about from about 10 g/ton to about 3000 g/ton, preferably from about 50 g/ton to about 2000 g/ton, and more preferably, from about 50 g/ton to about 800 g/ton. Some preferred dosages for various animals and indications are given below.

| Animal | Indications for Use | Dosage |
|---|---|---|
| Chickens | For an increased rate of weight gain and improved feed efficiency | 10–50 g/ton |
| Chickens | For control of infectious synovitis caused by *Mycoplasma synoviae*[1] | 100–200 g/ton |
| Chickens | For control of chronic respiratory disease (CRD) and air sac infection caused by *Mycoplasma gallisepticum* and *Escherichia coli*[1,2,3] | 200–400 g/ton |
| Chickens | For reduction of mortality due to *Escherichia coli* infections[2,4,5] | 500 g/ton |
| Turkeys | For an increased rate of weight gain and improved feed efficiency | 10–50 g/ton |
| Turkeys | For control of infectious synovitis caused by *Mycoplasma synoviae*[1] | 200 g/ton |
| Turkeys | For control of hexamitiasis caused by *Hexamita meleagrides*[1] | 400 g/ton |
| Turkeys | In turkey poults not over 4 weeks of age, for reduction of mortality due to paratyphoid caused by *Salmonella typhimurium* | 400 g/ton |
| Turkeys | For control of complicating bacterial organisms associated with bluecomb (transmissible enteritis, coronaviral enteritis)[1,2,3] | 25 mg/lb body wt/day |
| Sheep | For an increased rate of weight gain and improved feed efficiency | 20–50 g/ton |
| Sheep | For reducing the incidence of (vibrionic) abortion caused by *Campylobacter fetus* infection in breeding sheep[3] | 80 mg/ head/day |
| Swine | For an increased rate of weight gain and improved feed efficiency | 10–50 g/ton |
| Swine | For reducing the incidence of cervical lymphadenitis (jowl abscesses) caused by Group E. Streptococci | 50–100 g/ton |
| Swine | In breeding swine, for control of leptospirosis (reducing the instances of abortion and shedding of leptospirae) caused by *Leptospira pomona*[6] | 400 g/ton |
| Swine | For treatment of bacterial enteritis caused by *Escherichia coli* and *Salmonella choleraesuis* and bacterial pneumonia caused by caused *Pasteurella mulfocida*[3,7] | 10 mg/lb body wt/day |
| Calves | In calves up to 250 pounds, for an increased rate of weight gain and improved feed efficiency[8] | 0.1 mg/lb body wt/day |
| Calves | In calves 250–400 pounds, for an increased rate of weight gain and improved feed efficiency[8] | 25–70 mg/ head/day |
| Cattle | In growing cattle (over 400 pounds), for an increased rate of weight gain and improved feed efficiency and reduction of liver condemnation due to liver abscesses[3] | 70 mg/ head/day |
| Cattle | For the control of bacterial pneumonia associated with shipping fever complex | 350 mg/ head/day |
| Cattle | In beef cattle under 700 lbs, for control of active infection of anaplasmosis caused by *Anaplasma marginale* | 350 mg/ head/day |
| Cattle | In beef cattle over 700 lbs, for control of active infection of anaplasmosis caused by *Anaplasma marginale*[5] | 0.5 mg/lb body wt/day |

-continued

| Animal | Indications for Use | Dosage |
|---|---|---|
| Cattle | In calves,[8] beef, and non-lactating dairy cattle, for treatment of bacterial enteritis caused by *Escherichia coli* and bacterial pneumonia caused by *Pasteurella multocida* organisms[5,9] | 10 mg/lb body wt/day |

Figure 2:
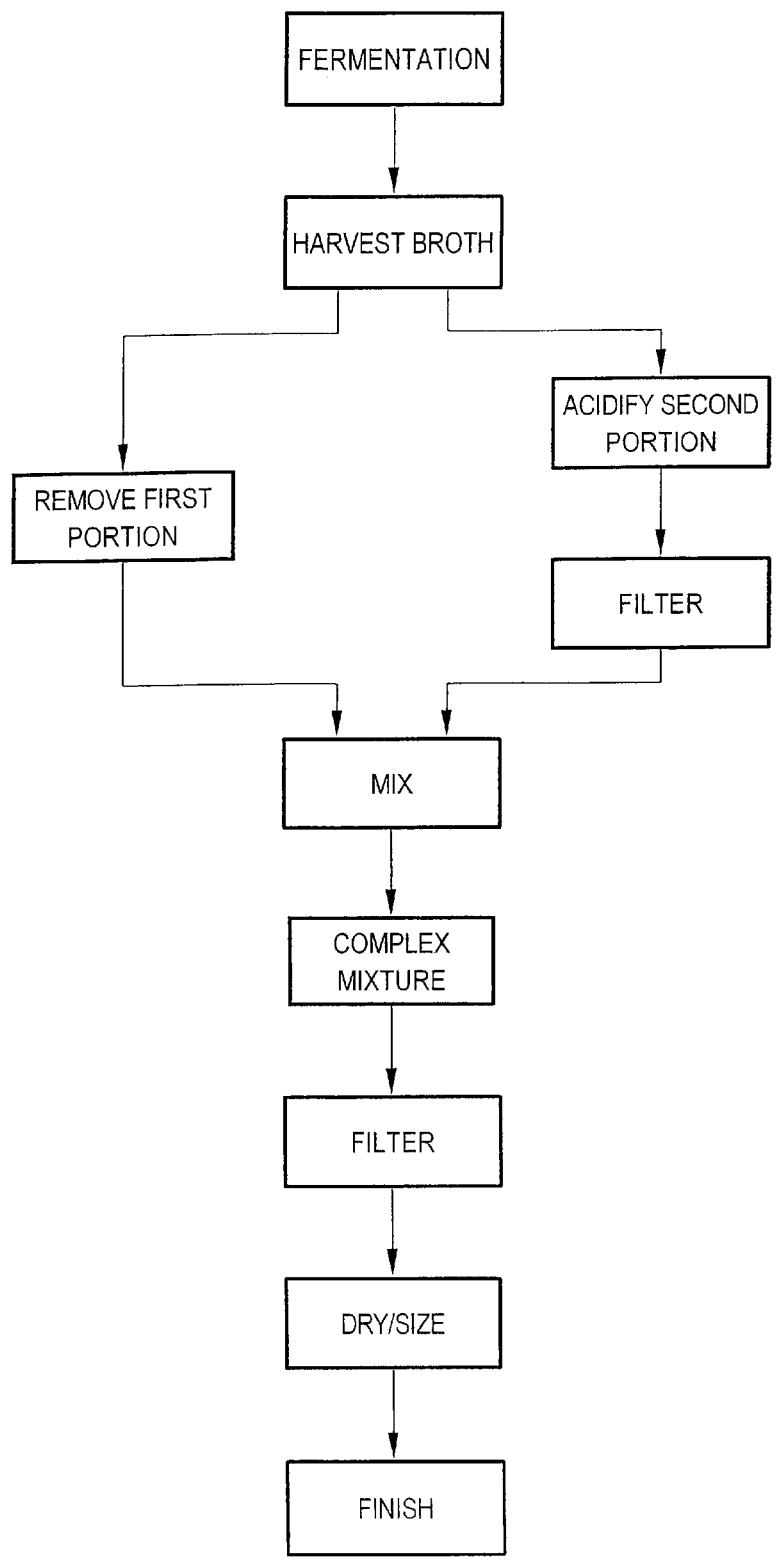
Figure 3:
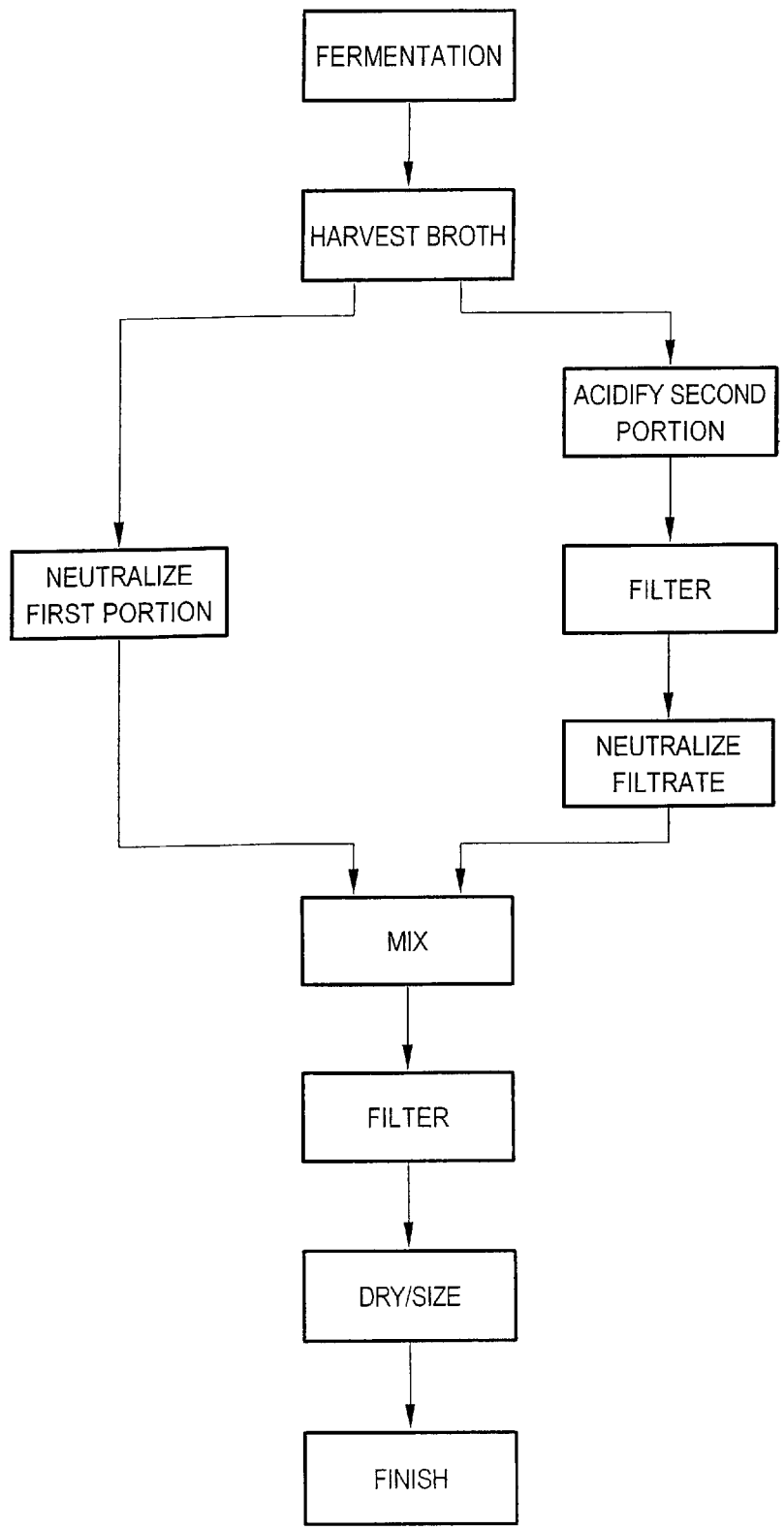
FIGS. 3 and 4 are flow charts outlining processes for preparing a chlortetracycline-containing animal feed composition in accordance with two embodiments of the present invention wherein the chlortetracycline is present in the form of the free base.
Figure 4:
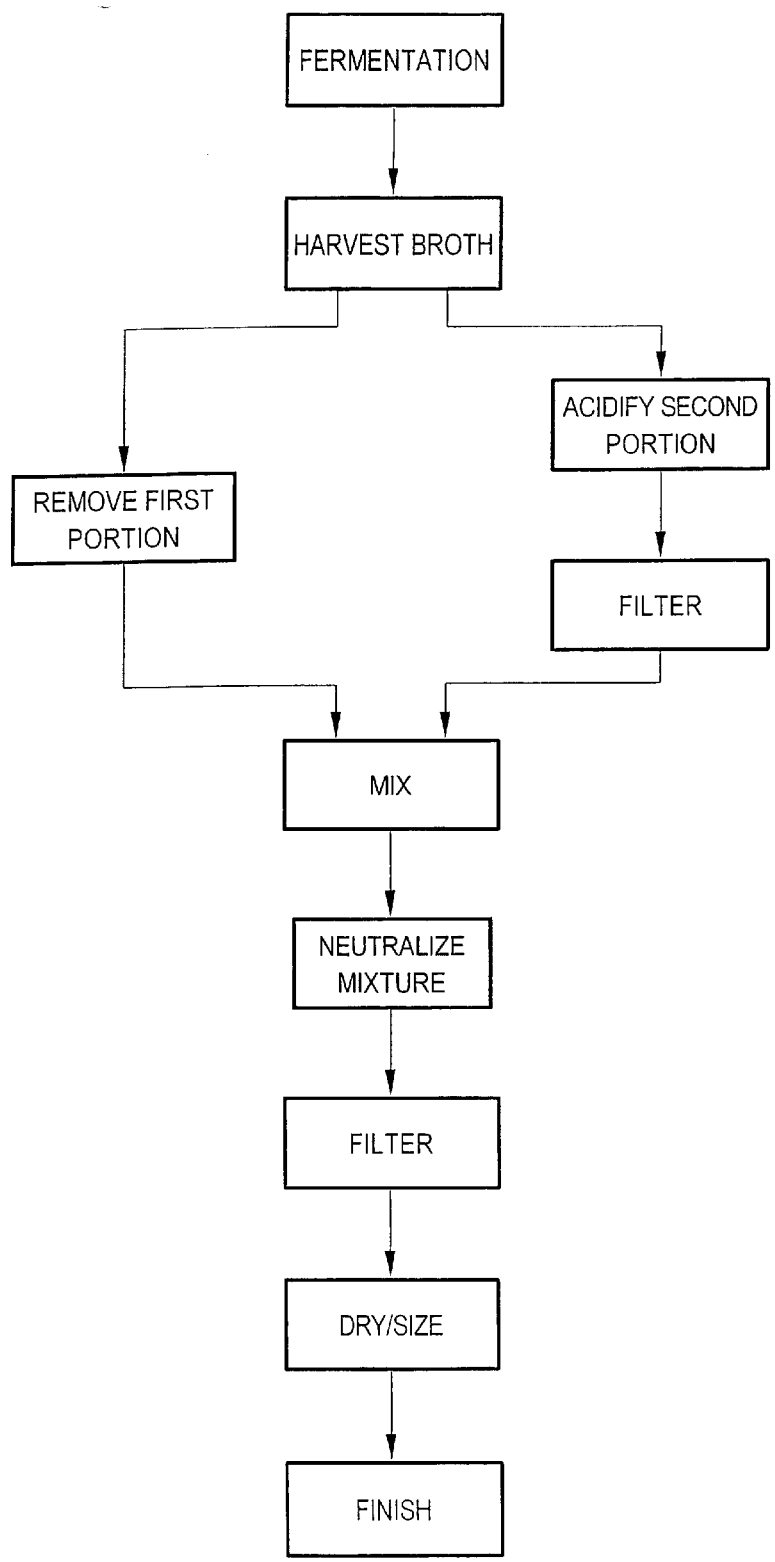

[1]Feed continuously for 7 to 14 days
[2]Do not feed to poultry producing eggs for human consumption
[3]Zero-day withdrawal period
[4]Feed for 5 days
[5]Withdraw 24 hours prior to slaughter
[6]Feed continuously for 14 days
[7]Feed for not more than 14 days
[8]A withdrawal period has not been established for this product in pre-ruminating calves
[9]Treat for not more than 5 days The following Examples are intended to illustrate but not to limit the invention. A flow chart outlining a process in accordance with the present invention illustrated by Examples 1–16 is shown in FIG. 1. A flow chart outlining a process in accordance with the present invention illustrated by Examples 1–7, 8A–12A, and 14–16 is shown in FIG. 2. A flow chart outlining a process in accordance with the present invention illustrated by Examples 1–8, 9B–13B, 14C–15C, and 16 is shown in FIG. 3. A flow chart outlining a process in accordance with the present invention illustrated by Examples 1–7, 8C–15C and 16 is shown in FIG. 4.

EXAMPLE 1

Raw Materials and Media Composition

A test tube is used to store the spore of the *Streptomyces aureofaciens* chlortetracycline strain. Washed sand is screened through an 80 mesh sieve. The sand is placed into a glass tube and sterilized at 121° C., 0.104 MPa for 30 minutes. After sterilization, the sand is dried and cooled. The strain spore of chlortetracycline is inoculated into a sterilized tube containing slant media using an inoculation needle under aseptic conditions. The tube is sealed with a cotton ball. The inoculated media is cultivated for 4–5 days at 30 to 40° C., preferably 35±1° C., under thermostatically controlled conditions. The media is cooled and kept in the refrigerator at 4° C. until ready for use.

EXAMPLE 2

Slant Media

The composition of the culture media is as follows:

| Ingredient | Preferred Material | Preferred Range (%) |
|---|---|---|
| Carbon Source | Wheat Bran | 3.0–3.5 |
| Activator | $MgSO_4$ | 0.004–0.006 |
| Nitrogen Source | $(NH_4)_2HPO_4$ | 0.01–0.02 |
| Activator | $K_2HPO_4$ | 0.008–0.012 |
| Solidifier | Agar | 0.05–0.10 |
| Moisturizer | Water | Remainder |

A single colony is selected from cultured media described above under aseptic conditions and inoculated on a slant media as described above. The inoculum is then cultivated for 4–5 days at 30 to 40° C., preferably 35±1° C., under thermostatically controlled conditions. After the growth of the spore, the well-grown slant is selected and kept in a refrigerator at between 3° C. to 5° C. until ready for use.

EXAMPLE 3

Seed Media

The composition of the seed media is as follows:

| Ingredient | Preferred Material | Preferred Range (%) |
|---|---|---|
| Carbon Source | Corn Starch | 3.0–4.0 |
| Nitrogen Source | Peanut Meal or Soybean Meal | 1.5–3.5 |
| Nitrogen Source | Peptone | 0.4–0.6 |
| Nitrogen Source | Yeast Powder | 0.4–0.8 |
| Nitrogen Source | $(NH_4)_2SO_4$ | 0.2–0.4 |
| Carbon Source & Buffer | $CaCO_3$ | 0.2–0.4 |
| Activator | NaCl | 0.1–0.3 |
| Activator | $KH_2PO_4$ | 0.02–0.04 |
| Defoamer | Vegetable Oil | 0.3–0.4 |
| Moisturizer | Water | 90.0–93.9 |

The seed culture media is prepared in a container tank and stirred until completely homogeneous. The media is fed into a seed tank through a sieve. Water is added and the tank is closed. The tank is sterilized with steam and cooled. The seed media is inoculated and aeration and agitation is started. The airflow rate is from 0.5 to 2.0 $m^3$ per minute per $m^3$ fermentation broth. The temperature is held at 25° C. to 35° C. for 24 to 36 hours. The pH should be about 6.0, the amino nitrogen content should be from 60–120 mg/100 mL, and chlortetracycline potency should be greater than 75 u/mL.

EXAMPLE 4

Fermentation Media

The composition of the media for fermentation tanks will consists of the following ingredients and respective ranges. The media is prepared and transferred to the fermentation tank.

| Ingredient | Preferred Material | Preferred Range (%) |
|---|---|---|
| Carbon Source | Corn Starch | 7.0–9.0 |
| Nitrogen Source | Peanut Meal or Soybean Meal | 3.0–3.5 |
| Nitrogen Source | Peptone | 0.4–0.6 |
| Nitrogen Source | Yeast Powder | 0.4–0.8 |
| Bio-Catalyst | α-amylase | 0.01–0.02 |
| Nitrogen Source | $(NH_4)_2SO_4$ | 0.5–1.0 |
| Carbon Source & Buffer | $CaCO_3$ | 0.4–0.7 |
| Activator | $KH_2PO_4$ | 0.02–0.03 |
| Activator | NaCl | 0.1–0.3 |
| Activator | $MgSO_4$ | 0.01–0.03 |
| Nitrogen Source | Corn-Steep Liquor | 1.2–1.8 |
| Defoamer | Vegetable Oil | 0.15–.025 |
| Moisturizer | Water | 86.8–82.0 |

EXAMPLE 5

Sugar Tank Composition

The sugar preparation added to the fermentation tank during fermentation is composed of the following:

| Ingredient | Preferred Material | Preferred Range (%) |
|---|---|---|
| Carbon Source | Starch | 40–50 |
| Nitrogen Source | Peanut Meal or Soybean Meal | 0–0.6 |
| Nitrogen Source | Corn-Steep Liquor | 1.0–2.5 |
| Bio-Catalyst | α-amylase | 0.05–0.08 |
| Carbon Source & Buffer | $CaCO_3$ | 0.4–0.8 |
| Activator | NaCl | 0.2–0.4 |

-continued

| Ingredient | Preferred Material | Preferred Range (%) |
| --- | --- | --- |
| Nitrogen Source | Peptone | 0–0.3 |
| Nitrogen Source | Yeast Powder | 0–0.3 |
| Activator | $CaCl_2$ | 0–0.3 |
| Defoamer | Vegetable Oil | 0.15–.025 |
| Moisturizer | Water | 44.5–58.2 |

EXAMPLE 6

Air Used During the Production Process

Air used during the fermentation process should be sterilized prior to be being injected to the fermentation or other media. The air is drawn into a compressor through a filter consisting of metallic net and foam rubber. Any impurities in the air, such as dirt, dust, sand, etc., are then removed. The air from the compressor should be cooled to about 15° C. to about 35° C. The cooled air is then ridded of oil and water by passing through an oil and water separator. The air is then heated to about 40° C. to about 50° C. The air is then passed through a filtration system. The filtered air is then fed to the seed and fermentor tanks for use in aeration in the fermentation process.

EXAMPLE 7

Fermentation

The fermentation culture media is pumped from the compounding pool into the fermentor. The media is sterilized by the introduction of steam. After the fermentation media has cooled, the seed culture media is pumped into the fermentor through a sterile tube. Cultivation then takes place. During fermentation, the temperature is maintained at 25° C. to 40° C., preferably about 28° C. to about 35° C., for 120 to 140 hours, with sterilized sugar media added as required with aeration. During fermentation, ammonia (for example, aqueous ammonia, about 20% or greater) is introduced into the fermentor as necessary to maintain pH at 5.5 to 6.3.

The following EXAMPLES 8 through 13 illustrate a first embodiment of harvesting the fermentation broth and recovering complexed chlortetracycline in accordance with the present invention.

EXAMPLE 8

Harvesting of Fermentation Broth

When the desired potency is reached, e.g., about 15,000 u/mg to about 30,000 u/m, or higher where a higher potency is desired, preferably about 25,000 u/mg to about 29,000 u/mg, the fermentation process is ended and the fermentation broth is discharged from the fermentation tank and divided into two portions. Discharge of the fermentation broth may be carried out by any convenient technique, such as using a pump, pressure, gravity, etc. A first portion is sent directly to a complexing tank for complexing and precipitation of the calcium complex of chlortetracycline. A second portion of the harvested broth is sent to an acidification tank for acidification and dilution. The ratio of the first portion of raw fermentation broth sent directly to the complexing tank for complexing and the second portion of the second portion of the raw fermentation broth removed for acidification preferably ranges from about 1:20 to about 20:1, and may be selected to give a desired concentration of chlortetracycline in the semi-finished product. In one embodiment, the ratio of the first portion to the second portion ranges from about 1:10 to about 10:1. In another embodiment, the ratio of the first portion to the second portion ranges from about 1:5 to about 5:1. In still another embodiment, the ratio of the first portion to the second portion ranges from about 1:3 to about 3:1. In yet another embodiment, the ratio of the first portion to the second portion ranges from about 1:2 to about 2:1. In another embodiment, the ratio of the first portion to the second portion ranges from about 2:3 to about 3:2. In yet another embodiment, the ratio of the first portion to the second portion is about 1:1.

EXAMPLE 9

Complexing First Portion of Raw Fermentation Broth

The first portion of the fermentation broth is sent to a complexing tank. The fermentation broth is optionally cooled, e.g., to below about 20° C. Calcium carbonate (about 0.1% to about 4%, preferably about 0.4 to about 1.0%, w/v, based on the volume of complexed fermentation broth) is added and aqueous ammonia or other suitable base is added to adjust the pH to a value of about 7.0 or greater, preferably from about 7.0 to about 9.0, and more preferably about 7.6 to about 7.8. The base is preferably aqueous ammonia having a concentration of about 10% or greater, preferably about 20% or greater.

EXAMPLE 10

Acidification of Second Portion of Raw Fermentation Broth

The second portion of the harvested broth is sent to an acidification tank and cooled, preferably from about 15–20° C. The acid used may be any mineral acid or sufficiently strong organic acid as are known to those skilled in the art. The acid is added in sufficient quantity to adjust the pH to about 4.0 or less, preferably about 3.0 or less, and most preferably about 2.0 or less. In a preferred embodiment, the acid is an acid that forms a pharmaceutically acceptable salt of chlortetracycline and most preferably is hydrochloric acid, hydrobromic acid, sulfuric acid, oxalic acid, or mixtures thereof. In an exemplary embodiment, oxalic acid (2.0% calculated based on total quantity of the harvested broth), is added while agitating and HCl is added to adjust the pH to about 1.1 to 1.3. Sodium ferrocyanide may be added in amount less than about 2.0% calculated based on total quantity of the harvested broth. In an exemplary embodiment, sodium ferrocyanide is added in amount of from about 0.1–0.2%, calculated based on total quantity of the harvested broth. Zinc sulfate may also be added in amount less than about 2.0% calculated based on total quantity of the harvested broth. In an exemplary embodiment, zinc sulfate is added in amount of from about 0.1–0.2%, calculated based on total quantity of the harvested broth. An aqueous solution of oxalic acid (pH<about 3.0, preferably from about 1.5 to about 1.8) is then added to dilute the acidified broth to obtain potency at about 10,000 unit/ml.

EXAMPLE 11

Filtration of Acidified Fermentation Broth

The acidified broth is pumped to a filter press or other means for separating the liquids. The filtrate containing the chlortetracycline hydrochloride is collected and may be sent directly for complexing or, optionally, may be and recirculated through the filter press for a second filtration prior to being passed on for complexing.

EXAMPLE 12

Complexing and Precipitation of Acidified Filtrate

The acidified filtrate is complexed in a manner similar to the first portion. Calcium carbonate (0.01 to about 10%, preferably about 0.1–2.0%, w/v, based on total volume of acidified broth) is added to the complexing tank containing the acidified broth. Aqueous ammonia or other suitable base is added while agitating to adjust the pH to a value of about 7.0 or greater, preferably about 7.0 to about 9.0, and more preferably about 7.6 to about 7.8. The temperature is maintained at about 5 to about 15° C. The base is preferably aqueous ammonia having a concentration of about 10% or greater, preferably about 20% or greater. Stirring is continued for about 1 hour to obtain a suspension of chlortetracycline calcium complex.

EXAMPLE 13

Mixing

The complexed fermentation broth obtained from the first portion of the raw fermentation broth and the chlortetracycline calcium complex obtained from the acidified and filtered broth (second portion) are mixed and the mixture is cooled to about 20° C. or less. The mixture is stirred until well mixed, e.g., for about 3 to about 30 minutes, preferably for about 5 to about 10 minutes. After mixing, the mixture is pumped to a filter press or other suitable means for filtration and separation.

The following EXAMPLES 8A through 12A illustrate a second embodiment of harvesting the fermentation broth and recovering complexed chlortetracycline in accordance with the present invention.

EXAMPLE 8A

Harvesting of Fermentation Broth

A chlortetracycline producing fermentation operation is performed as described in Examples 1–7, above. When the desired potency is reached, e.g., about 15,000 u/mg to about 30,000 u/mg, or higher where a higher potency is desired, preferably about 25,000 u/mg to about 29,000 u/mg, the fermentation process is ended and the fermentation broth is discharged from the fermentation tank and divided into two portions. Discharge of the fermentation broth may be carried out by any convenient technique, such as using a pump, pressure, gravity, etc. The first portion remains in its raw state and the second portion of the harvested broth is sent to an acidification tank for acidification. The first portion is either discharged and stored until treatment (acidification and filtration) of the second portion is completed, or, may remain in the fermentor until treatment of the second portion is completed. The ratio of the first and second portions of the second portion of the raw fermentation broth preferably ranges from about 1:20 to about 20:1, and may be selected to give a desired concentration of chlortetracycline in the semi-finished product. In one embodiment, the ratio of the first portion to the second portion ranges from about 1:10 to about 10:1. In another embodiment, the ratio of the first portion to the second portion ranges from about 1:5 to about 5:1. In still another embodiment, the ratio of the first portion to the second portion ranges from about 1:3 to about 3:1. In yet another embodiment, the ratio of the first portion to the second portion ranges from about 1:2 to about 2:1. In another embodiment, the ratio of the first portion to the second portion ranges from about 2:3 to about 3:2. In yet another embodiment, the ratio of the first portion to the second portion is about 1:1.

EXAMPLE 9A

Acidification of Second Portion of Raw Fermentation Broth

The second portion of the harvested broth (from Example 8A) is sent to an acidification tank and cooled, preferably from about 15–20° C. The acid used may be any mineral acid or sufficiently strong organic acid as are known to those skilled in the art. The acid is added in sufficient quantity to adjust the pH to about 4.0 or less, preferably about 3.0 or less, and most preferably about 2.0 or less. In a preferred embodiment, the acid is an acid that forms a pharmaceutically acceptable salt of chlortetracycline and most preferably is hydrochloric acid, sulfuric acid, and/or oxalic acid. In an exemplary embodiment, oxalic acid (2.0% calculated based on total quantity of the harvested broth), is added while agitating and HCl is added to adjust the pH to about 1.1 to 1.3. Sodium ferrocyanide may be added in amount less than about 2.0% calculated based on total quantity of the harvested broth. In an exemplary embodiment, sodium ferrocyanide is added in amount of from about 0.1–0.2%, calculated based on total quantity of the harvested broth. Zinc sulfate may also be added in amount less than about 2.0% calculated based on total quantity of the harvested broth. In an exemplary embodiment, zinc sulfate is added in amount of from about 0.1–0.2%, calculated based on total quantity of the harvested broth. An aqueous solution of oxalic acid (pH<about 3.0, preferably from about 1.5 to about 1.8) is then added to dilute the acidified broth to obtain potency at about 10,000 unit/ml.

EXAMPLE 10A

Filtration of Acidified Fermentation Broth

The acidified broth from Example 9A is pumped to a filter press or other means for separating the liquids. The filtrate containing the chlortetracycline hydrochloride is collected and may be sent directly to the complexing tank or, optionally, may be and recirculated through the filter press for a second filtration prior to being passed on to the complexing tank containing the first portion.

EXAMPLE 11A

Mixing

The first portion of the raw fermentation broth (from Example 8A) and the acidified and filtered broth containing chlortetracycline obtained from the second portion (from Example 10A) are mixed, and the mixture is optionally cooled to about 20° C. or less. The mixture is stirred until well mixed, e.g., for about 3 to about 30 minutes, preferably for about 5 to about 10 minutes.

EXAMPLE 12A

Complexing Mixture Containing the First Portion of Raw Fermentation Broth and Acidified Filtrate The mixture of raw fermentation broth and acidified filtrate fermentation from Example 11A broth is optionally cooled, e.g., to below about 20° C. Calcium carbonate (0.01 to about 10%, preferably about 0.1–2.0%, w/v, based on total volume of the mixture) is added to the complexing tank to complex the mixture. Aqueous ammonia or other suitable base is added while agitating to adjust the pH to a value of about 7.0 or greater, preferably about 7.0 to about 9.0, and more preferably about 7.6 to about 7.8. The temperature is maintained at about 5 to about 15° C. The pH adjusting base is preferably aqueous ammonia having a concentration of about 10% or greater, preferably about 20% or greater. Stirring is continued for about 1 hour to obtain a suspension of chlortetracycline calcium complex. After complexing, the complexed mixture is pumped to a filter press or other suitable means for filtration and separation.

The following Examples refer to treatment of the complexed chlortetracycline mixture obtained in accordance with this teaching to produce a semi-finished or finished animal feed additive.

EXAMPLE 14

Filtration

The complexed mixture (obtained by either Example 13A or Example 12B) is pumped to a filter press, or other means for separating the liquid, for filtration. The wet cake is discharged from the filter press and collected by any convenient means, e.g., into trays, fluid bed, etc., for drying.

EXAMPLE 15

Drying/Milling

The wet filter cake containing the filtration solids obtained is Example 14 is dried at elevated temperature, for example, in an oven by using hot air flow, a fluid bed, or another suitable drying method as described above. When the moisture content reaches from about 2% to about 10%, preferably about 4% to about 8%, and most preferably about 4% to about 6%, the drying is ended and the dried product is removed from the dryer. In one embodiment, the drying temperature is preferably less than about 100° C., preferably from about 60° C. to about 90° C., and more preferably about 80° C. or less.

The dried product so produced is milled and sized, for example, by grinding, milling, pulverizing, screening, etc., to produce a semi-finished granular product having a desired particle size. The particles are then screened to produce the semi-finished product having desired particle size. In one embodiment, the particle size ranges from about 180 $\mu$m (80 mesh) to about 2 mm (10 mesh). In one embodiment, the particle size from about 212 $\mu$m (70 mesh) to about 1 mm (18 mesh). In one embodiment, the particles have a size of about 10 mesh or coarser. Particles larger than the desired size may be further milled. Particles smaller than the desired particle size may be collected and used in other applications, or may be recycled to subsequent batches of harvested fermentation broth to increase chlortetracycline concentration in subsequent batches.

The following Examples 9B through 13B illustrate a further embodiment of the present invention wherein the chlortetracycline is present in the free base form.

EXAMPLE 9B

Precipitating First Portion of Raw Fermentation Broth

A chlortetracycline-containing fermentation broth is produced and harvested as described in Examples 1–8. The first portion of the fermentation broth is sent to a precipitating tank. The fermentation broth is optionally cooled, e.g., to below about 20° C. Aqueous ammonia or other suitable base is added to neutralize the fermentation broth. The base is added in an amount to adjust the pH to a value of about 7.0 or greater, preferably from about 7.0 to about 9.0, and more preferably about 7.6 to about 7.8. The base is preferably aqueous ammonia having a concentration of about 10% or greater, preferably about 20% or greater.

EXAMPLE 10B

Acidification of Second Portion of Raw Fermentation Broth

The second portion of the harvested broth is sent to an acidification tank and cooled, preferably from about 15–20° C. The acid used may be any mineral acid or sufficiently strong organic acid as are known to those skilled in the art. The acid is added in sufficient quantity to adjust the pH to about 4.0 or less, preferably about 3.0 or less, and most preferably about 2.0 or less. In a preferred embodiment, the acid is an acid that forms a pharmaceutically acceptable salt of chlortetracycline and most preferably is hydrochloric acid, hydrobromic acid, sulfuric acid, oxalic acid, or mixtures thereof. In an exemplary embodiment, oxalic acid (2.0% calculated based on total quantity of the harvested broth), is added while agitating and HCl is added to adjust the pH to about 1.1 to 1.3. Sodium ferrocyanide may be added in amount less than about 2.0% calculated based on total quantity of the harvested broth. In an exemplary embodiment, sodium ferrocyanide is added in amount of from about 0.1–0.2%, calculated based on total quantity of the harvested broth. Zinc sulfate may also be added in amount less than about 2.0% calculated based on total quantity of the harvested broth. In an exemplary embodiment, zinc sulfate is added in amount of from about 0.1–0.2%, calculated based on total quantity of the harvested broth. An aqueous solution of oxalic acid (pH<about 3.0, preferably from about 1.5 to about 1.8) is then added to dilute the acidified broth to obtain potency at about 10,000 unit/ml.

EXAMPLE 11B

Filtration of Acidified Fermentation Broth

The acidified broth from Example 10B is pumped to a filter press or other means for separating the liquids. The filtrate containing the chlortetracycline hydrochloride is collected and may be sent directly for precipitation or, optionally, may be and recirculated through the filter press for a second filtration prior to being passed on for precipitation.

EXAMPLE 12B

Precipitation of Acidified Filtrate

The acidified filtrate is precipitated in a manner similar to the first portion. Aqueous ammonia or other suitable base is added to yield chlortetracycline in the free base form. The base is added to the tank containing the acidified broth while agitating to adjust the pH to a value of about 7.0 or greater, preferably about 7.0 to about 9.0, and more preferably about 7.6 to about 7.8. The temperature is maintained at about 5 to about 15° C. The base is preferably aqueous ammonia having a concentration of about 10% or greater, preferably about 20% or greater. Stirring is continued for about 1 hour to obtain a suspension of chlortetracycline in the free base form.

EXAMPLE 13B

Mixing

The precipitated fermentation broth obtained in Example 9B and the chlortetracycline suspension obtained in Example 12B are mixed and the mixture is cooled to about 20° C. or less. The mixture is stirred until well mixed, e.g., for about 3 to about 30 minutes, preferably for about 5 to about 10 minutes. After mixing, the mixture is pumped to a filter press or other suitable means for filtration and separation.

The following EXAMPLES 8C through 12C illustrate yet another embodiment of the present invention wherein the feed supplements contain chlortetracycline in its free base form.

EXAMPLE 8C

Harvesting of Fermentation Broth

A chlortetracycline producing fermentation operation is performed as described in Examples 1–7, above, and the fermentation broth is harvested and divided into two portions as described above in Example 8A.

EXAMPLE 9C

Acidification of Second Portion of Raw Fermentation Broth

The second portion of the harvested broth (from Example 8C) is acidified as described in Example 9A, above.

EXAMPLE 10C

Filtration of Acidified Fermentation Broth

The acidified broth from Example 9C is filtered and the filtrate collected as described in Example 10A, above.

EXAMPLE 11C

Mixing

The first portion of the raw fermentation broth (from Example 8C) and the acidified and filtered broth containing chlortetracycline obtained from the second portion (from Example 10C) are mixed, and the mixture is optionally cooled to about 20° C. or less. The mixture is stirred until well mixed, e.g., for about 3 to about 30 minutes, preferably for about 5 to about 10 minutes.

EXAMPLE 12C

Precipitating Mixture Containing the First Portion of Raw Fermentation Broth and Acidified Filtrate The mixture of raw fermentation broth and acidified filtrate fermentation from Example 11C broth is optionally cooled, e.g., to below about 20° C. Aqueous ammonia or other suitable base is added to neutralize the mixture and yield chlortetracycline in the free base form. The mixture while agitating to adjust the pH to a value of about 7.0 or greater, preferably about 7.0 to about 9.0, and more preferably about 7.6 to about 7.8. The temperature is maintained at about 5 to about 15° C. The pH adjusting base is preferably aqueous ammonia having a concentration of about 10% or greater, preferably about 20% or greater. Stirring is continued for about 1 hour to obtain a suspension of the free base of chlortetracycline. The mixture is pumped to a filter press or other suitable means for filtration and separation.

EXAMPLE 14C

Filtration

The mixture (obtained by either Example 13B or Example 12C) is pumped to a filter press, or other means for separating the liquid, for filtration. The wet cake is discharged from the filter press and collected by any convenient means, e.g., into trays, fluid bed, etc., for drying.

EXAMPLE 15C

Drying/Milling

The wet filter cake containing the filtration solids obtained is Example 14C is dried and sized as described above in Example 15.

EXAMPLE 16

Finishing

Samples of the semi-finished product obtained in Example 15 or Example 15C are drawn and analyzed for active ingredient content, moisture and ash content. The process in accordance with this teaching typically produces a semi-finished chlortetracycline product having a chlortetracycline content of from about 5% to about 70%. In one embodiment, the semi-finished product has a chlortetracycline concentration of from about 10% to about 66%. In yet another embodiment, the semi-finished product has a chlortetracycline concentration of from about 11% to about 65%. In yet another embodiment, the semi-finished product has a chlortetracycline concentration of from about 13% to about 60%. In yet another embodiment, the semi-finished product has a chlortetracycline concentration of from about 15% to about 55%. In yet another embodiment, the semi-finished product has a chlortetracycline concentration of from about 17% to about 50%. In yet another embodiment, the semi-finished product has a chlortetracycline concentration of from about 19% to about 45%. In yet another embodiment, the semi-finished product has a chlortetracycline concentration of from about 20% to about 45%. In yet another embodiment, the semi-finished product has a chlortetracycline concentration of from about 30% to about 44%.

The semi-finished product may then be standardized to a desired potency by adding one or more of an edible feed material, a mineral product, and an oil in ratios of a sufficient quantity to produce the desired potency. In admixing the ingredients, the solid ingredients may be admixed, for example, with a feed blender, by hand, and so forth. In one embodiment, the semi-finished product and edible feed material are placed in a blender and the oil is sprayed over the carriers during the mixing process.

The edible feed material, mineral product, semi-finished product, and oil are preferably combined in the following concentrations by weight:

| Ingredient | Concentration |
| --- | --- |
| Edible feed material | 0.0 to 90% |
| Mineral product | 0.0 to 89% |
| Semi-finished product | 2.4 to 98% |
| Oil or fat | 0.0 to 15% |

In a preferred embodiment, the raw material is assayed and the quantities of edible feed material and mineral product are adjusted to provide a standardized concentration or potency of the antibiotic.

Suitable edible feed materials include chaffs, silage, meals, pellets, concentrates or the like formed from grains, nuts, beans and other plant parts, including for example, grain products such as corn, rice, wheat, milo, rice bran, other straws or grasses rich in crude fibrous material, ground corn cobs, oil seeds and by products, soybean mill run, wheat middlings, wheat bran oat groats, oat bran, barley, alfalfa meal chaff or silage, wheat germ, corn germ meal, soybean grits, corn gluten feed, soybean meal, coconut meal, soya bean meal, peanut meal, corn cob meal, linseed meal, cottonseed meal, alfalfa leaf meal, rice hulls, and the like. Other edible feed materials include dried beet pulp, dried molasses beet pulp, dried potato pulp, dried citrus pulp, dried brewers grains, corn distillers dried grains, oat mill feed, heat treated soy mill feed, etc. The edible feed material is preferably rice hull.

If an oil is to be used in preparing the finished feed supplements according to the present invention, any non-toxic oil or fat may be used in the formulation. Suitable oils include, for example, mineral oil, waxes, cotton seed oil, palm oil, peanut oil, corn oil, sesame oil, coconut oil, soybean oil, grapeseed oil, linseed oil, lard, tallow, and the like. The oil is preferably mineral oil. It is not necessary that oil, if it is to be added, be added during the finishing stage and may be added earlier in the process, such as during the fermentation stage. The oil may be used during fermentation as an assimilable source of carbon and thus, some of the excess oil may be carried over into the semi-finished product.

The mineral product may be one or more mineral products suitable for use in an animal feed or feed supplement or other veterinary use. Exemplary mineral products include but are not limited to ammonium sulfate, animal bone ash, animal bone charcoal, animal bone charcoal (spent), animal bone meal (cooked or boiled), animal bone meal (steamed), animal bone phosphate, calcite (ground), calcium carbonate, calcium carbonate (precipitated), calcium chloride, calcium formate, calcium gluconate, calcium hydroxide, calcium iodate, calcium iodobehenate, calcium oxide, calcium periodate, calcium sulfate, chalk (precipitated), chalk rock (ground), clam shells (ground), cobalt acetate, cobalt carbonate, cobalt chloride, cobalt choline citrate complex, cobalt glucoheptonate, cobalt gluconate, cobalt oxide, cobalt sulfate, copper carbonate, cuprous chloride, cupric chloride, copper choline citrate complex, cupric gluconate, cupric hydroxide, cupric orthophosphate, cuprous oxide, cupric oxide, cupric sulfate, cuprous iodide, diiodosalicylic acid, ethylene diamine dihydroiodide, ferric ammonium citrate, ferric chloride, ferric choline citrate complex, ferric formate, ferric phosphate, ferric pyrophosphate, ferric sulfate, ferrous carbonate, ferrous chloride, ferrous fumarate, ferrous gluconate, ferrous glycine complex, ferrous sulfate, gypsiferrous shale, ferric oxide, reduced iron, limestone (ground), limestone (dolomitic ground), limestone (magnesium ground), magnesium carbonate, magnesium chloride, magnesium hydroxide, magnesium phosphate, magnesium oxide, magnesium-mica, magnesium sulfate, manganese acetate, manganous carbonate, manganous chloride, manganous citrate, manganous gluconate, manganese orthophosphate, manganese phosphate dibasic, manganous sulfate, manganous oxide, metal amino acid complexes, copper amino acid complex, zinc amino acid complex, magnesium amino acid complex, iron amino acid complex, cobalt amino acid complex, calcium amino acid complex, calcium amino acid complex, potassium amino acid complex, manganese amino acid complex, copper lysine complex, zinc lysine complex, ferric methionine complex, manganese methionine complex, zinc methionine complex, metal amino acid chelates, calcium amino acid chelate, cobalt amino acid chelate, copper amino acid chelate, iron amino acid chelate, magnesium amino acid chelate, manganese amino acid chelate, zinc amino acid chelate, metal polysaccharide complex, copper polysaccharide complex, iron polysaccharide complex, zinc polysaccharide complex, magnesium polysaccharide complex, metal proteinate, copper proteinate, zinc proteinate, magnesium proteinate, iron proteinate, cobalt proteinate, manganese proteinate, calcium proteinate, oyster shell flour, ammonium polyphosphate solution, calcium phosphate, diammonium phosphate, dicalcium phosphate, disodium phosphate, monoammonium phosphate, monocalcium phosphate, monosodium phosphate, phosphoric acid, defluorinated phosphate, rock phosphate (soft), rock phosphate (ground), rock phosphate (ground, low fluorine), sodium hexametaphosphate, sodium tripolyphosphate, tribasic sodium phosphate, tricalcium phosphate, potassium bicarbonate, potassium carbonate, potassium citrate, potassium chloride, potassium hydroxide, potassium iodate, potassium iodide, potassium sulfate, sodium chloride, sodium chloride (iodized), shell flour, sodium acid pyrophosphate, sodium bicarbonate, sodium carbonate, sodium iodate, sodium iodide, sodium molybdate, sodium selenate, sodium selenite, sodium sesquicarbonate, sodium sulfate, sulfur, thymol iodide, zinc acetate, zinc carbonate, zinc chloride, zinc chloride diammine complex, zinc oxide, zinc sulfate, bone phosphate, copper acetate, basic copper chloride ($Cu_2(OH)_3Cl$), and chromium picolinate.

In one embodiment, the mineral product is limestone. By "limestone" is meant not only naturally occurring form calcium carbonate such chalk, dolomite, etc., but also is intended to encompass veterinary, agricultural, and technical grade calcium carbonate. Of course, higher grades of calcium carbonate may be employed as well.

In one embodiment, where an edible feed material and/or mineral product are utilized, they are also granular in nature and are sized so as to be substantially the same size as the particles of the semi-finished product, thereby minimizing their separation during handling.

In one embodiment, the resulting composition has a chlortetracycline concentration of from about 5% to about 70%. In another embodiment, the resulting composition has a chlortetracycline concentration of from about 10% to about 66%. In yet another embodiment, the resulting composition has a chlortetracycline concentration of from about 11% to about 65%. In yet another embodiment, the resulting composition has a chlortetracycline concentration of from about 13% to about 60%. In yet another embodiment, the resulting composition has a chlortetracycline concentration of from about 15% to about 55%. In yet another embodiment, the resulting composition has a chlortetracycline concentration of from about 17% to about 50%. In yet another embodiment, the resulting composition has a chlortetracycline concentration of from about 19% to about 45%. In yet another embodiment, the resulting composition has a chlortetracycline concentration of from about 20% to about 45%. In yet another embodiment, the resulting composition has a chlortetracycline concentration of from about 30% to about 44%. In some of the presently preferred embodiments, the animal feed supplement in accordance with this teaching provides chlortetracycline calcium complex in an amount having an activity equivalent to 50, 60, 70, 80, 90, 100, or 200 grams of chlortetracycline hydrochloride per pound of animal feed supplement.

The animal feed premixes according to the present invention may also contain additional ingredients as typically used in animal husbandry, such as coccidiostats, additional antibiotics, minerals, vitamins, growth promoters, antioxidants, anthelmintics, preservatives, colorings, flavorings, or other dietary supplements.

Figure 5:
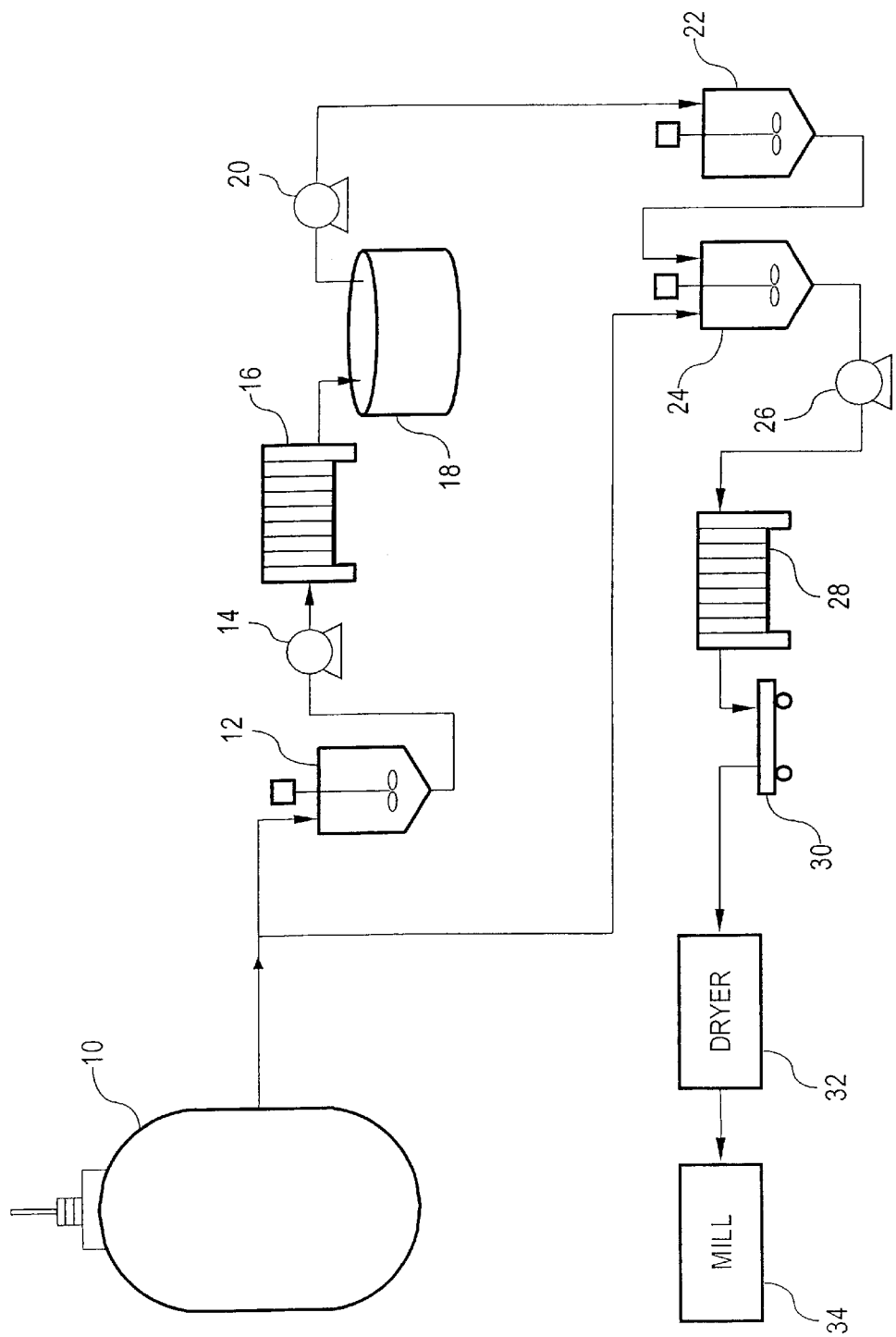
FIGS. 5 and 6 are schematic diagrams of two systems designed for carrying out procedures of the present invention.
Figure 6:
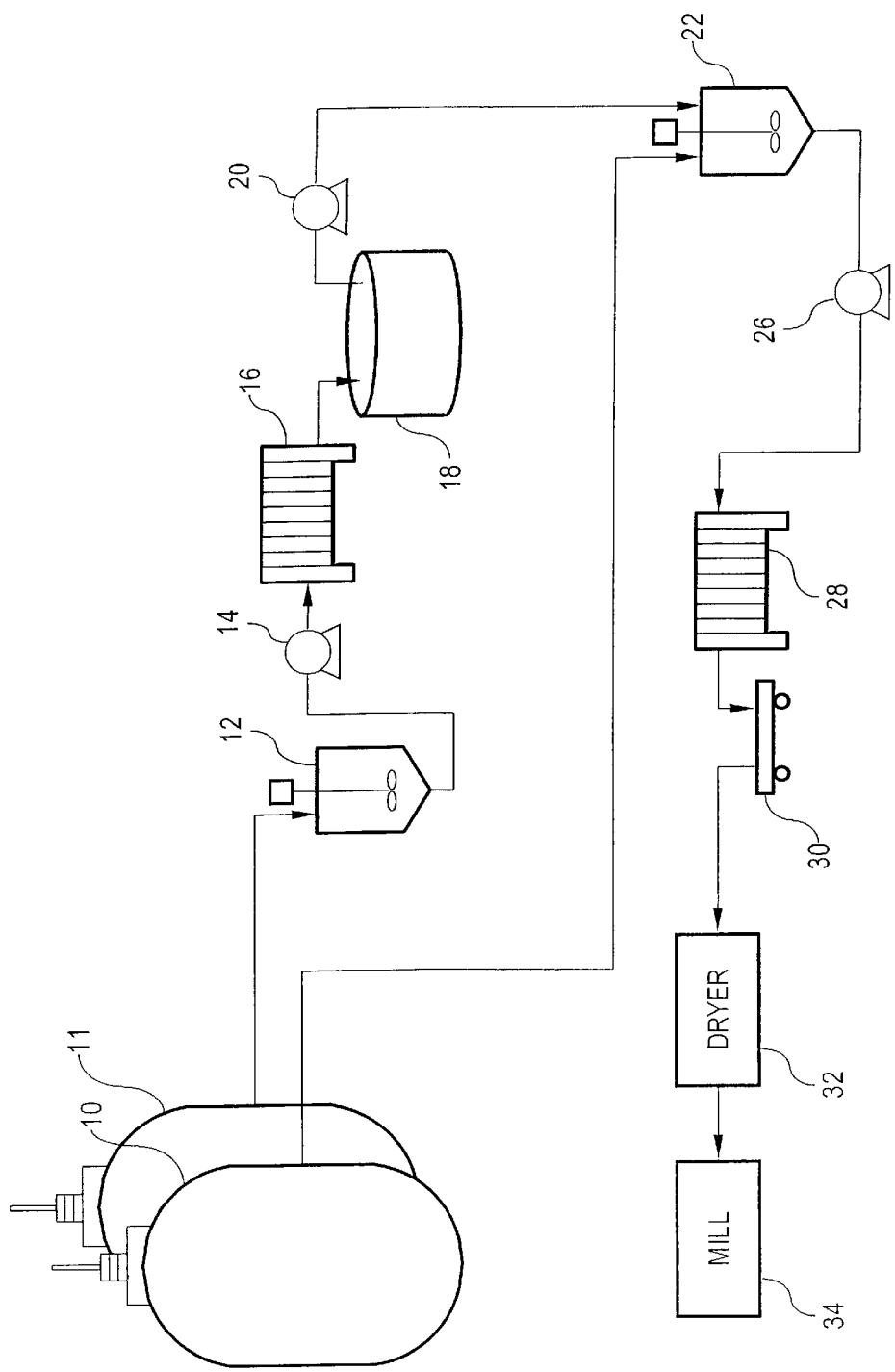

In order to provide for comprehension of the invention, for illustrative purposes and without a restrictive scope, a description is furnished as to the details of particular embodiments of the invention, making reference to FIGS. 5 and 6, in which diagramed arrangements of two exemplary systems designed for carrying out the processes in accordance with the present invention are shown.

As is shown in FIG. 5, the system comprises a fermentor 10 for producing chlortetracycline as is generally known in the art. Following the fermentation process, it is shown in the drawing that the fermentation broth is discharged from fermentor 10 so that a first portion of the harvested fermentation broth is routed directly to mixing tank 24 for precipitation of the chlortetracycline (either as the free base or as a complex) and a second portion is routed to acidification tank 12 for acidification. Alternatively, as stated above, rather than dividing a single fermentation batch into two portions, the two portions may be harvested from separate fermentors (see FIG. 6) or separate fermentation batches from the same fermentor. The acidified portion is pumped via pump 14 to filter press 16 and the filtrate is collected in filtrate pool 18. The filtrate may optionally be recirculated to filter 16 for one or more additional filtrations and the filtrate is pumped via pump 20 to precipitation tank 22 for precipitation, either as the free base, or as a complex. The precipitated filtrate is then passed on to mixing tank 24 for admixture with the previously treated fermentation broth. If the acidified filtration broth is filtered only once, filtrate pool 18 may be omitted and the filtrate may be passed on directly from filter press 16 to tank 22. The combined mixture is then pumped via pump 26 through filter press 28. The wet filter cake is removed from filter press 28 and is transported by whatever means are convenient, such as trolley 30, to dryer 32 to produce the dry product then to an appropriate milling or sizing apparatus 34 for preparation of the semi-finished product.

The circuit, as shown in FIG. 5, comprises a plurality of like or similar devices, e.g., a plurality of filter presses, mixing tanks, and pumps. Thus, in an alternative embodiment, this device affords the possibility of replacing a plurality of like or similar devices with a single unit by alternating its use.

Referring now to FIG. 6, the system comprises a plurality of fermentors 10 and 11 for producing chlortetracycline as is generally known in the art. Following the fermentation process, it is shown in the drawing that the fermentation broth is discharged from fermentor 10 and routed directly to mixing tank 22 and the fermentation broth from fermentor 11 is routed to acidification tank 12 for acidification. Alternatively, as stated above, rather than employing separate fermentors 10 and 11, a single fermentation batch may be divided into two portions (see FIG. 5), the two fermentation batches may be harvested from separate fermentation batches produced in the same fermentor. The acidified portion is pumped via pump 14 to filter press 16 and the filtrate is collected in filtrate pool 18. The filtrate may optionally be recirculated to filter 16 for one or more additional filtrations and the filtrate is pumped via pump 20 to precipitation tank 22 and mixed with the raw fermentation broth discharged from fermentor 10. If the acidified filtration broth is filtered only once, filtrate pool 18 may be omitted and the filtrate may be passed on directly from filter press 16 to tank 22. The mixture is treated to precipitate the chlortetracycline, either as the free base, or as a complex and is then pumped via pump 26 through filter press 28. The wet filter cake is removed from filter press 28 and is transported by whatever means are convenient, such as trolley 30, to dryer 32 to produce the dry product then to an appropriate milling or sizing apparatus 34 for preparation of the semi-finished product.

The circuit, as shown in FIG. 6, comprises a plurality of like or similar devices, e.g., a plurality of fermentors, filter presses, mixing tanks, and pumps. Thus, in an alternative embodiment, this device affords the possibility of replacing a plurality of like or similar devices with a single unit by alternating its use.

The description above should not be construed as limiting the scope of the invention, but as merely providing illustrations to some of the presently preferred embodiments of this invention. In light of the above description and examples, various other modifications and variations will now become apparent to those skilled in the art without departing from the spirit and scope of the present invention as defined by the appended claims. Accordingly, the scope of the invention should be determined solely by the appended claims and their legal equivalents. All references cited herein are incorporated by reference in their entireties.

What is claimed is:

1. An animal feed composition comprising complexed chlortetracycline in a solid carrier, said solid carrier comprising fermentation solids derived from a fermentation broth produced by fermentation of an organism producing chlortetracycline, wherein said animal feed composition is prepared by:

(a) providing first and second quantities of fermentation broth comprising chlotetracycline, said first and second quantities of fermentation broth produced by fermentation of an organism producing chlortetracycline, said first and second quantities of fermentation broth comprising fermentation solids and liquids;

(b) adjusting the pH of the first quantity of fermentation broth to a value of about 7 or greater to produce fermentation broth containing chlortetracycline;

(c) lowering the pH of said second quantity of fermentation broth to a level sufficient to dissolve the chlortetracycline in said second quantity of fermentation broth;

(d) removing solids from said pH-adjusted second quantity of fermentation broth and collecting liquid containing dissolved chlortetracycline;

(e) adjusting the pH of said liquid containing dissolved chlortetracycline to a value of about 7 or greater to produce a suspension;

(f) mixing said fermentation broth containing complexed chlortetracycline from step (b) and said suspension from step (e);

(g) removing liquids from the mixture to produce a chlortetracycline containing fermentation product having a low moisture content; and (h) sizing said low moisture content fermentation product to produce a particulate chlortetracycline-containing fermentation product having a predetermined particle size or range of particle sizes.

2. A composition according to claim 1, wherein adjusting the pH of the first quantity of fermentation broth to a value of about 7 or greater to produce fermentation broth containing chlortetracycline includes adding a chlortetracycline complexing compound in an amount sufficient to produce fermentation broth containing complexed chlortetracycline.

3. A composition according to claim 1, wherein adjusting the pH of the first quantity of fermentation broth to a value of about 7 or greater to produce fermentation broth containing chlortetracycline produces a fermentation broth containing chlortetracycline in free base form.

4. A composition according to claim 1, wherein adjusting the pH of said liquid containing dissolved chlortetracycline to a value of about 7 or greater to produce a suspension includes adding a chlortetracycline complexing compound in an amount sufficient to produce a suspension of complexed chlortetracycline.

5. A composition according to claim 1, wherein adjusting the pH of said liquid containing dissolved chlortetracycline to a value of about 7 or greater to produce a suspension produces a suspension of chlortetracycline in free base form.

6. A composition according to claim 1, wherein the ratio of said first quantity of fermentation broth to said second quantity of fermentation broth is from about 1:10 to about 10:1.

7. A composition according to claim 1, wherein the ratio of said first quantity of fermentation broth to said second quantity of fermentation broth is from about 1:5 to about 5:1.

8. A composition according to claim 1, wherein the ratio of said first quantity of fermentation broth to said second quantity of fermentation broth is from about 1:3 to about 3:1.

9. A composition according to claim 1, wherein the first quantity of fermentation broth and the second quantity of fermentation broth are from the same fermentation batch.

10. A composition according to claim 1, wherein the first quantity of fermentation broth and the second quantity of fermentation broth are from different fermentation batches.

11. A composition according to claim 2, wherein the chlortetracycline complexing compound added to said first quantity of fermentation broth is calcium carbonate.

12. A composition according to claim 1, wherein the pH of the first quantity of fermentation broth is adjusted by the addition of aqueous ammonia.

13. A composition according to claim 1, wherein the pH of the first quantity of fermentation broth is adjusted to a value of from about 7.5 to about 8.0.

14. A composition according to claim 1, wherein the pH of the second quantity of fermentation broth is adjusted by adding a mineral acid.

15. A composition according to claim 1, wherein the pH of the second quantity of fermentation broth is adjusted by adding one or more acids selected from the group consisting of oxalic acid, hydrochloric acid, and sulfuric acid.

16. A composition according to claim 1, wherein the pH of the second is quantity of fermentation broth is adjusted to a value of about 4.0 or less.

17. A composition according to claim 1, wherein the pH of the second quantity of fermentation broth is adjusted to a value of about 2.0 or less.

18. A composition according to claim 1, wherein the pH of the second quantity of fermentation broth is adjusted to a value of about 1.0 to about 1.3.

19. A composition according to claim 2, wherein said chlortetracycline complexing compound added to said liquid containing dissolved chlortetracycline is calcium carbonate and the pH of said liquid containing dissolved chlortetracycline is adjusted by the addition of aqueous ammonia.

20. A composition according to claim 5, wherein the pH of said liquid containing dissolved chlortetracycline is adjusted by the addition of aqueous ammonia.

21. A composition according to claim 1, wherein the pH of said liquid containing dissolved chlortetracycline is adjusted to a pH of from about 7.5 to about 8.0.

22. A composition according to claim 1, wherein the removal of liquids in step g) utilizes one or more of the following: a filter press, centrifugal filter, rotary vacuum filter, oven, tray dryer, tunnel dryer, spray dryer, spray granulator, fluid bed dryer, shelf dryer, drum dryer, rotary dryer, microwave dryer, and contact dryer.

23. A composition according to claim 1, wherein the removal of liquids in step (g) utilizes at least one of: a filter press, a centrifuge, and an oven.

24. A composition according to claim 1, wherein said filter cake is dried to a moisture content of from about 2% to about 12%.

25. A composition according to claim 1, wherein said filter cake is dried to a moisture content of from about 2% to about 6%.

26. A composition according to claim 1, wherein said low moisture content fermentation product comprises chlortetracycline in an amount from about 30% to about 75%.

27. A composition according to claim 1, wherein said solid having low moisture content comprises chlortetracycline in an amount from about 35% to about 65%.

28. A composition according to claim 1, wherein said solid having low moisture content comprises chlortetracycline in an amount from about 44% to about 55%.

29. A composition according to claim 1, wherein said particles are in the form of a powder, meal, pellets, granules, or tablets.

30. A composition according to claim 1, wherein said particles have a diameter of from about 150 $\mu$m to about 2 mm.

31. A composition according to claim 1, wherein said particles are produce without any compression or compaction step.

32. A composition according to claim 1, wherein said particles are produced with a compression or compaction step.

33. A composition according to claim 1, further comprising the step of blending said particulate chlortetracycline-containing fermentation product with at least one diluent selected from the group consisting of an edible feed material, a mineral product, and an oil.

34. A composition according to claim 33, further comprising the step of admixing said granules with a nonmedicated animal feedstuff.

35. A composition according to claim 33, wherein said edible feed material is rice hulls.

36. A composition according to claim 33, wherein said mineral product is limestone.

37. A composition according to claim 33, wherein said oil is mineral oil.

38. An animal feed composition comprising complexed chlortetracycline in a solid carrier, said solid carrier comprising fermentation solids derived from a fermentation broth produced by fermentation of an organism producing chlortetracycline, wherein said animal feed composition is prepared by:
   (a) providing first and second quantities of fermentation broth comprising chlortetracycline, said first and second quantities of fermentation broth produced by fermentation of an organism producing chlortetracycline, said first and second quantities of fermentation broth comprising fermentation solids and liquids;
   (b) lowering the pH of said second quantity of fermentation broth to a level sufficient to dissolve the chlortetracycline in said second quantity of fermentation broth;
   (c) removing solids from said pH-adjusted second quantity of fermentation broth and collecting liquid containing dissolved chlortetracycline;

(d) mixing said liquid containing dissolved chlortetracycline with said first quantity of fermentation broth to produce a mixture;

(e) adjusting the pH of the mixture of step (d) to a value of about 7 or greater;

(f) removing liquids from the mixture of step (e) to produce a complexed chlortetracycline-containing fermentation product having a low moisture content; and (h) sizing said low moisture content fermentation product to produce a particulate chlortetracycline-containing fermentation product having a predetermined particle size or range of particle sizes.

39. A composition according to claim 38, wherein adjusting the pH of the mixture of step (d) to a value of about 7 or greater includes adding a chlortetracycline complexing compound in an amount sufficient to complex the chlortetracycline in the mixture.

40. A composition according to claim 38, wherein the pH of the mixture of step (d) is adjusted to a value of about 7 or greater to form a mixture containing chlortetracycline in the free base formula.

41. A composition according to claim 38, wherein the ratio of said first quantity of fermentation broth to said second quantity of fermentation broth is from about 1:10 to about 10:1.

42. A composition according to claim 38, wherein the ratio of said first quantity of fermentation broth to said second quantity of fermentation broth is from about 1:5 to about 5:1.

43. A composition according to claim 38, wherein the ratio of said first quantity of fermentation broth to said second quantity of fermentation broth is from about 1:3 to about 3:1.

44. A composition according to claim 38, wherein the first quantity of fermentation broth and the second quantity of fermentation broth are from the same fermentation batch.

45. A composition according to claim 38, wherein the first quantity of fermentation broth and the second quantity of fermentation broth are from different fermentation batches.

46. A composition according to claim 39, wherein the chlortetracycline complexing compound added to said first quantity of fermentation broth is calcium carbonate.

47. A composition according to claim 38, wherein the pH of the mixture is adjusted in step (e) by the addition of aqueous ammonia.

48. A composition according to claim 38, wherein the pH of the mixture is adjusted in step (e) to a value of from about 7.5 to about 8.0.

49. A composition according to claim 38, wherein the pH of the second quantity of fermentation broth is adjusted by adding a mineral acid.

50. A composition according to claim 38, wherein the pH of the second quantity of fermentation broth is adjusted by adding one or more acids selected from the group consisting of oxalic acid, hydrochloric acid, and sulfuric acid.

51. A composition according to claim 38, wherein the pH of the second quantity of fermentation broth is adjusted to a value of about 4.0 or less.

52. A composition according to claim 38, wherein the pH of the second quantity of fermentation broth is adjusted to a value of about 2.0 or less.

53. A composition according to claim 38, wherein the pH of the second quantity of fermentation broth is adjusted to a value of about 1.0 to about 1.3.

54. A composition according to claim 38, wherein the removal of liquids in step (g) utilizes one or more of the following: a filter press, centrifugal filter, rotary vacuum filter, oven, tray dryer, tunnel dryer, spray dryer, spray granulator, fluid bed dryer, shelf dryer, drum dryer, rotary dryer, microwave dryer, and contact dryer.

55. A composition according to claim 33, wherein the removal of liquids in step (g) utilizes at least one of: a filter press, a centrifuge, and an oven.

56. A composition according to claim 33, wherein said filter cake is dried to a moisture content of from about 2% to about 12%.

57. A composition according to claim 33, wherein said filter cake is dried to a moisture content of from about 2% to about 6%.

58. A composition according to claim 33, wherein said low moisture content fermentation product comprises chlortetracycline in an amount from about 30% to about 75%.

59. A composition according to claim 33, wherein said solid having low moisture content comprises chlortetracycline in an amount from about 35% to about 65%.

60. A composition according to claim 33, wherein said solid having low moisture content comprises chlortetracycline in an amount from about 189% to about 55%.

61. A composition according to claim 33, wherein said particles are in the form of a powder, meal, pellets, granules, or tablets.

62. A composition according to claim 33, wherein said particles have a diameter of from about 150 $\mu$m to about 2 mm.

63. A composition according to claim 33, wherein said particles are produced without any compression or compaction step.

64. A composition according to claim 33, wherein said particles are produced with a compression or compaction step.

65. A composition according to claim 33, further comprising the step of blending said particulate chlortetracycline-containing fermentation product with at least one diluent selected from the group consisting of an edible feed material, a mineral product, and an oil.

66. A composition according to claim 65, further comprising the step of admixing said granules with a nonmedicated animal feedstuff.

67. A composition according to claim 65, wherein said edible feed material is rice hulls.

68. A composition according to claim 65, wherein said mineral product is limestone.

69. A composition according to claim 65, wherein said oil is mineral oil.

70. An animal feed composition comprising complexed chlortetracycline in a solid carrier, said solid carrier comprising fermentation solids derived from a fermentation broth produced by fermentation of an organism producing chlortetracycline, wherein said animal feed composition is prepared by:

(a) providing first and second quantities of fermentation broth comprising chlortetracycline, said first and second quantities of fermentation broth produced by fermentation of an organism producing chlortetracycline, said first and second quantities of fermentation broth comprising fermentation solids and liquids;

(b) adjusting the pH of the first quantity of fermentation broth to a value of about 7 or greater and adding a chlortetracycline complexing compound in an amount sufficient to produce fermentation broth containing complexed chlortetracycline;

(c) lowering the pH of said second quantity of fermentation broth to a level sufficient to dissolve the chlortetracycline in said second quantity of fermentation broth;

(d) removing solids from said pH-adjusted second quantity of fermentation broth and collecting liquid containing dissolved chlortetracycline;

(e) adjusting the pH of said liquid containing dissolved chlortetracycline to a value of about 7 or greater and adding a chlortetracycline complexing compound in an amount sufficient to produce a suspension of complexed chlortetracycline;

(f) mixing said fermentation broth containing complexed chlortetracycline from step (b) and said suspension of complexed chlortetracycline from step (e);

(g) removing liquids from the mixture of step (f) to produce a complexed chlortetracycline-containing fermentation product having a low moisture content; and (h) sizing said low moisture content fermentation product to produce a particulate chlortetracycline-containing fermentation product having a predetermined particle size or range of particle sizes.

71. A composition according to claim 70, wherein the ratio of said first quantity of fermentation broth to said second quantity of fermentation broth is from about 1:10 to about 10:1.

72. A composition according to claim 70, wherein the ratio of said first quantity of fermentation broth to said second quantity of fermentation broth is from about 1:5 to about 5:1.

73. A composition according to claim 70, wherein the ratio of said first quantity of fermentation broth to said second quantity of fermentation broth is from about 1:3 to about 3:1.

74. A composition according to claim 70, wherein the first quantity of fermentation broth and the second quantity of fermentation broth are from the same fermentation batch.

75. A composition according to claim 70, wherein the first quantity of fermentation broth and the second quantity of fermentation broth are from different fermentation batches.

76. A composition according to claim 70, wherein the chlortetracycline complexing compound added to said first quantity of fermentation broth is calcium carbonate.

77. A composition according to claim 70, wherein the pH of the first quantity of fermentation broth is adjusted by the addition of aqueous ammonia.

78. A composition according to claim 70, wherein the pH of the first quantity of fermentation broth is adjusted to a value of from about 7.5 to about 8.0.

79. A composition according to claim 70, wherein the pH of the second quantity of fermentation broth is adjusted by adding a mineral acid.

80. A composition according to claim 70, wherein the pH of the second quantity of fermentation broth is adjusted by adding one or more acids selected from the group consisting of oxalic acid, hydrochloric acid, and sulfuric acid.

81. A composition according to claim 70, wherein the pH of the second quantity of fermentation broth is adjusted to a value of about 4.0 or less.

82. A composition according to claim 70, wherein the pH of the second quantity of fermentation broth is adjusted to a value of about 2.0 or less.

83. A composition according to claim 70, wherein the pH of the second quantity of fermentation broth is adjusted to a value of about 1.0 to about 1.3.

84. A composition according to claim 70, wherein said chlortetracycline complexing compound added to said liquid containing dissolved chlortetracycline is calcium carbonate and the pH of said liquid containing dissolved chlortetracycline is adjusted by the addition of aqueous ammonia.

85. A composition according to claim 70, wherein the pH of said liquid containing dissolved chlortetracycline is adjusted to a pH of from about 7.5 to about 8.0.

86. A composition according to claim 70, wherein the removal of liquids in step (g) utilizes one or more of the following: a filter press, centrifugal filter, rotary vacuum filter, oven, tray dyer, tunnel dryer, spray dryer, spray granulator, fluid bed dryer, shelf dryer, drum dryer, rotary dryer, microwave dryer, and contact dryer.

87. A composition according to claim 70, wherein the removal of liquids in step (g) utilizes at least one of: a filter press, a centrifuge, and an oven.

88. A composition according to claim 70, wherein said filter cake is dried to a moisture content of from about 2% to about 12%.

89. A composition according to claim 70, wherein said filter cake is dried to a moisture content of from about 2% to about 6%.

90. A composition according to claim 70, wherein said low moisture content fermentation product comprises chlortetracycline in an amount from about 30% to about 75%.

91. A composition according to claim 70, wherein said solid having low moisture content comprises chlortetracycline in an amount from about 35% to about 65%.

92. A composition according to claim 70, wherein said solid having low moisture content comprises chlortetracycline in an amount from about 44% to about 55%.

93. A composition according to claim 70, wherein said particles are in the form of a powder, meal, pellets, granules, or tablets.

94. A composition according to claim 70, wherein said particles have a diameter of from about 150 $\mu$m to about 2 mm.

95. A composition according to claim 70, wherein said particles are produced without any compression or compaction step.

96. A composition according to claim 70, wherein said particles are produced with a compression or compaction step.

97. A composition according to claim 70, further comprising the step of blending said particulate chlortetracycline-containing fermentation product with at least one diluent selected from the group consisting of an edible feed material, a mineral product, and an oil.

98. A composition according to claim 97, further comprising the step of admixing said granules with a nonmedicated animal feedstuff.

99. A composition according to claim 97, wherein said edible feed material is rice hulls.

100. A composition according to claim 97, wherein said mineral product is limestone.

101. A composition according to claim 97, wherein said oil is mineral.

102. A composition according to claim 1, wherein the fermentation product has a sufficient antibiotic activity to treat an animal.

103. A composition according to claim 38, wherein the fermentation product has a sufficient antibiotic activity to treat an animal.

104. A composition according to claim 70, wherein the fermentation product has a sufficient antibiotic activity to treat an animal.

* * * * *